(12) United States Patent
Owen et al.

(10) Patent No.: US 8,535,250 B2
(45) Date of Patent: Sep. 17, 2013

(54) METHOD AND APPARATUS TO DETECT THE FRAGMENTATION OF KIDNEY STONES BY MEASURING ACOUSTIC SCATTER

(75) Inventors: Neil Owen, Seattle, WA (US); Michael Bailey, Seattle, WA (US); Oleg Sapozhinikov, Seattle, WA (US)

(73) Assignee: University of Washington Through Its Center for Commercialization, Seattle, WA (US)

( * ) Notice: Subject to any disclaimer, the term of this patent is extended or adjusted under 35 U.S.C. 154(b) by 1648 days.

(21) Appl. No.: 11/872,668

(22) Filed: Oct. 15, 2007

(65) Prior Publication Data

US 2008/0091125 A1    Apr. 17, 2008

Related U.S. Application Data

(60) Provisional application No. 60/829,510, filed on Oct. 13, 2006.

(51) Int. Cl.
*A61B 8/00* (2006.01)
*A61N 7/00* (2006.01)

(52) U.S. Cl.
USPC ........... 601/4; 601/2; 600/437; 600/439; 600/407

(58) Field of Classification Search
USPC ............. 600/439, 552, 586, 437; 601/4, 601/2; 606/127, 128; 367/155, 157, 178, 367/180
See application file for complete search history.

(56) References Cited

U.S. PATENT DOCUMENTS

| | | |
|---|---|---|
| 3,606,879 A | 9/1971 | Estes |
| 4,375,818 A | 3/1983 | Suwaki et al. |
| 4,665,751 A | 5/1987 | Huschelrath |
| 4,899,733 A | 2/1990 | DeCastro et al. ............. 128/7 |
| 4,942,878 A * | 7/1990 | Dory ............................. 601/4 |

(Continued)

FOREIGN PATENT DOCUMENTS

WO    WO 2009/049148    4/2009

OTHER PUBLICATIONS

Schafer et al. "Design of a miniature in-vivo shock wave hydrophone," Ultrasonics Symposium, 1990. Proceedings., IEEE 1990, vol., No., pp. 1623-1626 vol. 3, Dec. 4-7, 1990. doi: 10.1109/ULTSYM.1990.171643.*

(Continued)

*Primary Examiner* — Unsu Jung
*Assistant Examiner* — Phong K Huynh
(74) *Attorney, Agent, or Firm* — Kilpatrick Townsend and Stockton LLP

(57) ABSTRACT

During shock wave therapy, a determination is made that a kidney stone has begun to fracture, and then a progress of its fragmentation is assessed. This determination can reduce the number of shock waves used to disintegrate kidney stones, and thereby reduce dose-dependent tissue damage. The identification of fracture is possible through the detection and analysis of resonant acoustic scattering, which is the radiation caused by reverberations within a stone particle that is struck by a shock wave. The scattering frequency can provide both an indication that the kidney stone has fragmented, and an indication of the relative sizes of the fragments. Related concepts employ displacement measurements of kidney stones/fragments to provide both an indication that the kidney stone has fragmented, and an indication of the relative sizes of the fragments. Such techniques can be combined with vibroacoustography based gating that better targets the stone.

20 Claims, 10 Drawing Sheets

(56) References Cited

U.S. PATENT DOCUMENTS

| | | | |
|---|---|---|---|
| 4,976,255 A * | 12/1990 | Reichenberger et al. | 601/4 |
| 5,209,234 A * | 5/1993 | LaRocca | 601/4 |
| 6,567,688 B1 * | 5/2003 | Wang | 600/437 |
| 6,902,528 B1 | 6/2005 | Garibaldi et al. | |
| 2003/0040737 A1 | 2/2003 | Merril et al. | 606/1 |
| 2005/0033314 A1 | 2/2005 | Sakurai et al. | 606/127 |
| 2007/0123518 A1 | 5/2007 | Epshtein | 514/221 |

OTHER PUBLICATIONS

Sapozhnikov et al. "Detecting Fragmentation of Kidney Stones in Lithotripsy by Means of Shock Wave Scattering". 5th International Symposium on Therapeutic Ultrasound, Oct. 27-29, 2005, Published online May 2006. http://proceedings.aip.org/resource/2/apcpcs/829/1?isAuthorized=no.*

Bailey, Michael R., Yuri A. Pishchalnikov, Oleg A. Sapozhnikov, Robin O. Cleveland, James A. McAteer, Nathan A. Miller, Irina V. Pishchalnikova, Bret A. Connors, Lawrence A. Crum, and Andrew P. Evan. "Cavitation Detection During Shock-Wave Lithotripsy" Ultrasound in Med. & Biol., vol. 31, No. 9, pp. 1245-1256, Copyright 2005.

Bohris, Christian, Thomas Bayer, and Christian Lechner. "Hit/Miss Monitoring of ESWL by Spectral Doppler Ultrasound," Ultrasound in Med & Biol., vol. 29, No. 5, pp. 705-712, Copyright 2003.

Chang, C.C., S.M. Liang, Y.R. Pu, C.H. Chen, I. Manousakas, T.S. Chen, C.L. Kuo, F.M. Yu, and Z.F. Chu. "In Vitro Study of Ultrasound Based Real-Time Tracking of Renal Stones for Shock Wave Lithotripsy: Part 1," The Journal of Urology, vol. 166, Jul. 28-32, 2001.

Cleveland, Robin O., and Oleg A. Sapozhnikov. "Modeling elastic wave propagation in kidney stones with application to shock wave lithotripsy," J. Acoust. Soc. Am. 118 (4), pp. 2667-2676, Oct. 2005.

Fedele, F., A.J. Coleman, T.G. Leighton, P.R. White, and A.M. Hurrell. "Development of a new diagnostic sensor for Extra-corporeal Shock-Wave Lithotripsy," Journal of Physics: Conference Series 1 (2004), pp. 134-139. Copyright 2004.

McAteer, J.A., M.R. Bailey, J.C. Williams, Jr., R.O. Cleveland, and A.P. Evan. "Strategies for improved shock wave lithotripsy," Minerva Urologica E Nefrologica, vol. 57, N. 4. pp. 271-287, Dec. 2005.

Orkisz, M., M. Bourlion, G. Gimenez, and T.A. Flam. "Real-time target tracking applied to improve fragmentation of renal stones in extra-corporeal lithotripsy," Machine Vision and Applications (1999) 11: 138-144.

Owen, Neil R., Michael R. Bailey, Adam Maxwell, Brian MacConaghy, Tatiana D. Khokhlova, and Lawrence A. Crum. "Vibro-acoustography for targeting kidney stones during lithotripsy," J. Acoust. Soc. Am., vol. 116, No. 4, Pt. 2, p. 2509, Oct. 2004.

Owen, Neil R., Michael R. Bailey, and Lawrence A. Crum. "Characterization of a vibro-acoustography system designed to detect kidney stones during lithotripsy," J. Acout. Soc. Am., vol. 117, No. 4, Pt. 2, p. 2588, Apr. 2005.

Sapozhnikov, O.A., R.O. Cleveland, M.R. Bailey, and L.A. Crum. "Modeling of Stresses Generated by Lithotripter Shock Wave in Cylindrical Kidney Stone," Proc. Of ISTU3, ed. By J.Y. Chapelon and C. Lafon, INSERM, Lyon, 2003, pp. 323-328.

Goldberg et al., "Endoluminal Sonography of the Urinary Tract: Preliminary Observations", Am. J. Roentgenology, vol. 156, Jan. 1991, pp. 99-103.

Chuong et al., "Acoustic and Mechanical Properties of Renal Calculi: Implications in Shock Wave Lithotripsy", Journal of Endourology, vol. 7, No. 6, 1993, pp. 437-444.

* cited by examiner

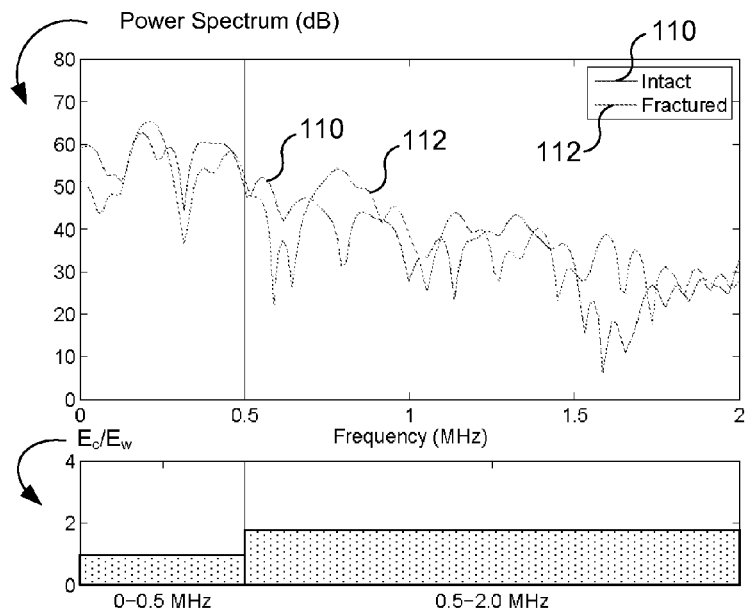
*FIG. 11C*
*FIG. 11D*
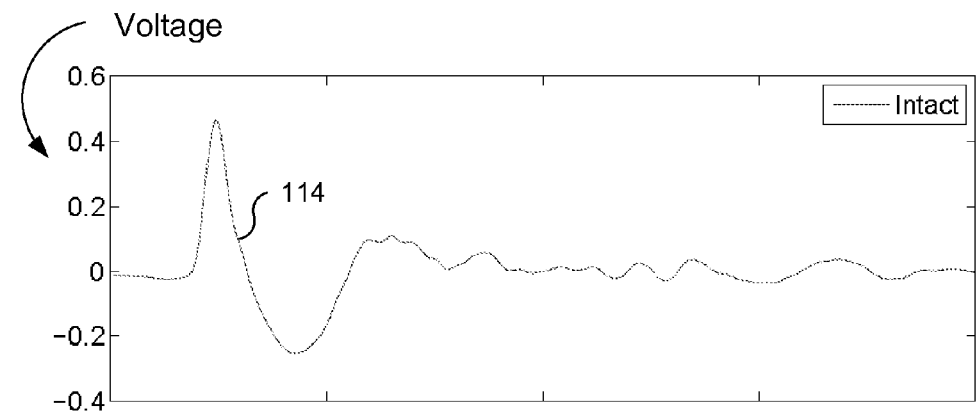
*FIG. 12A*
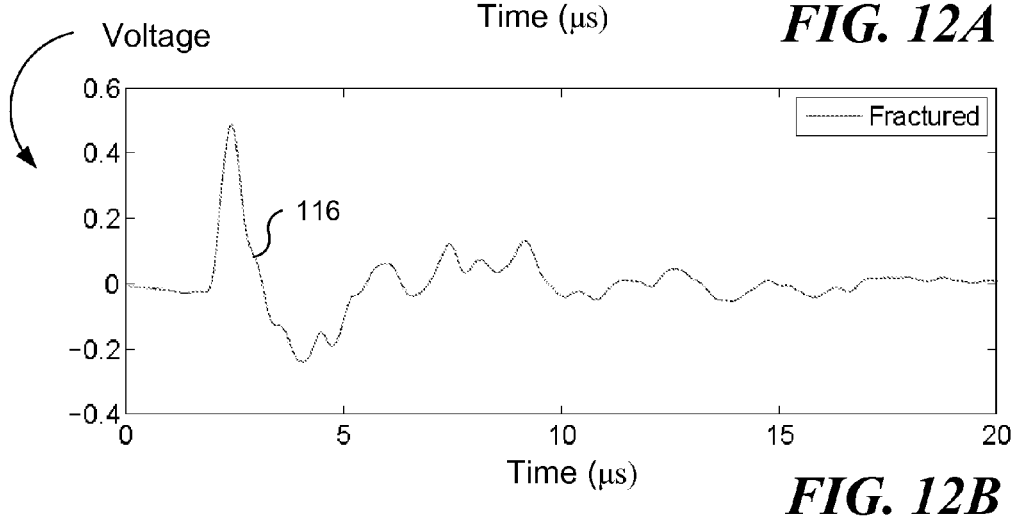
*FIG. 12B*

FIG. 16B
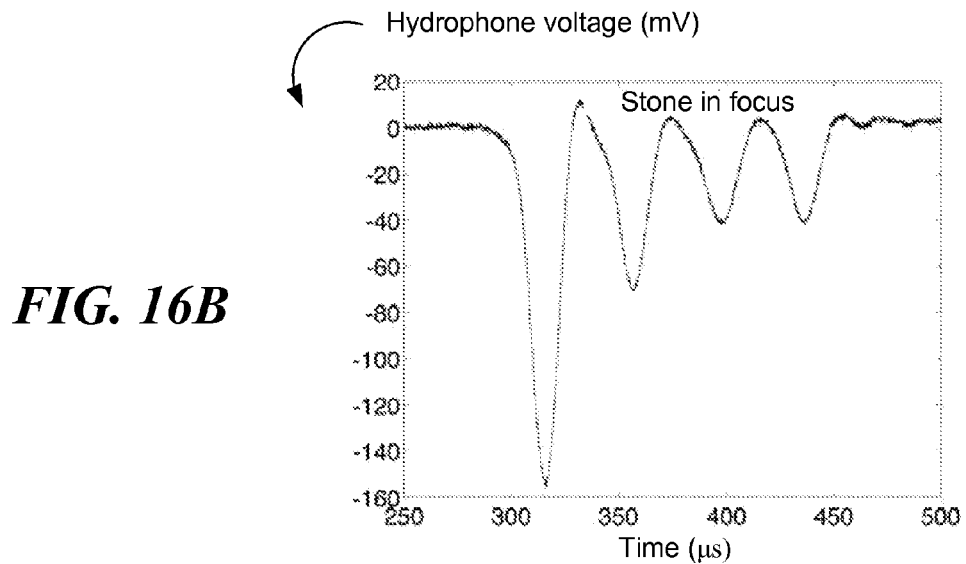
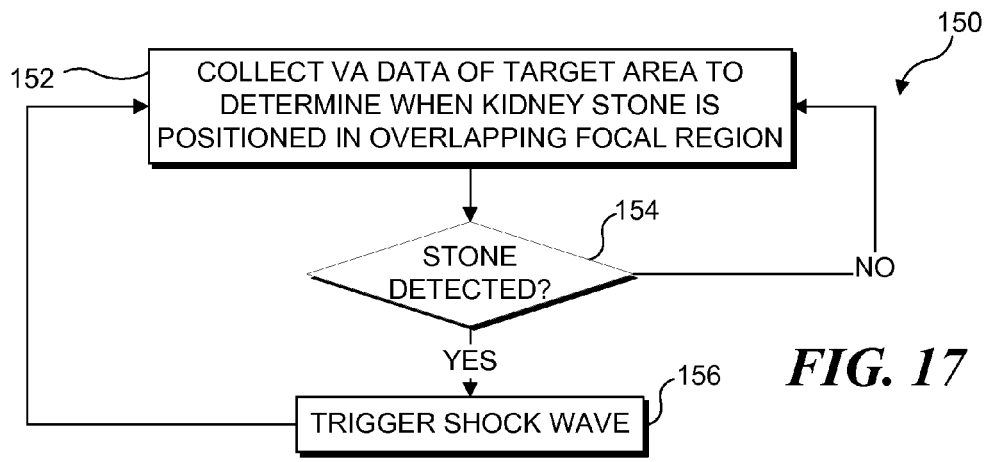
FIG. 17
| | Density ($kg/m^3$) | Sound Speed ($m/s$) | $\mu$ (GPa) | $\lambda$ (GPa) |
|---|---|---|---|---|
| Glass | 2300 | 5600 | 25 | 23 |
| Epoxy | 1430 | 2720 | - | - |
| Aluminum | 2700 | 6300 | 24 | 52 |
| Water | 1000 | 1500 | - | - |
FIG. 18

METHOD AND APPARATUS TO DETECT THE FRAGMENTATION OF KIDNEY STONES BY MEASURING ACOUSTIC SCATTER

RELATED APPLICATIONS

This application is based on a prior copending provisional application Ser. No. 60/829,510, filed on Oct. 13, 2006, the benefit of the filing date of which is hereby claimed under 35 U.S.C. §119(e).

GOVERNMENT RIGHTS

This invention was made with government support under a grant (DK43881) awarded by the National Institutes of Health, and a grant (SMS00402) awarded by the National Space Biomedical Research Institute. The government has certain rights in the invention.

BACKGROUND

Shock wave therapy of kidney stones, also known as shock wave lithotripsy (SWL), is a medical procedure in which focused acoustic shock waves are used to pulverize kidney stones into pieces that are sufficiently small to pass naturally from the body. It is termed a non-invasive procedure because the shock waves are generated outside the body, i.e., acoustic waves are transferred into the body through a coupling medium. However, SWL is not a benign procedure, since it is known that shock waves can cause acute and chronic complications to kidneys and other tissues. Further, tissue damage is dose-dependent, where dose is measured in part by the number of shock waves applied during a treatment session. The fragmentation of kidney stones is difficult to assess during SWL, and there is little unambiguous feedback available to a physician regarding the extent of fragmentation.

It would be desirable to provide physicians techniques that enable the fragmentation of kidney stones to be evaluated in order to determine when sufficient number of shock waves have been administered, so as to minimize the dose provided to the patient, thereby minimizing any negative effects.

SUMMARY

One goal of this technology is, during SWL, to identify when a kidney stone begins to break, and then assess the progress of fragmentation. This approach can reduce the number of shock waves used to disintegrate kidney stones, and thereby reduce dose-dependent tissue damage. The identification of stone fracture is possible through the detection and analysis of resonant acoustic scattering waves, which is the radiation caused by reverberations from a kidney stone particle after it is struck by a shock wave. Therefore, some of the concepts disclosed herein encompass a measurement device to detect the acoustic scatter, and a signal processing method to identify fragmented kidney stones based on the acoustic scatter.

Significantly, resonant acoustic scattering can be used to determine both when the kidney stone begins to fragment, and when the kidney stone is fully comminuted (i.e., all of the fragments are sufficiently small in size as to be able to pass through the urinary tract). When the shock wave interacts with the stone, the stone vibrates, and an acoustic sensor detects the frequency of those vibrations. The vibrations are a function of internal stresses in the kidney stone, where internal stress waves bounce back and forth across the dimensions of the kidney stone. These vibrations increase in frequency as the stone gets smaller (similar to small bells ringing with a higher pitch than large bells).

It should be recognized that the disclosure provided herein encompasses a plurality of related concepts. These concepts include, but are not limited to, the following aspects.

A first aspect of the concepts disclosed herein is a method for detecting the fragmentation of a kidney stone during shock wave therapy. Such a method will be extremely useful to clinicians during shock wave therapy, because prior art methods do not provide satisfactory indications of kidney stone fragmentation. While some clinicians are able to accurately interpret images of kidney stones during therapy to determine whether fragmentation of the kidney stone has occurred, most clinicians are not able to conclusively make that determination based on such images. The method corresponding to this first novel aspect will provide clinicians an empirical technique to conclusively evaluate the fragmentation of a kidney stone.

In this method, a resonant acoustic scattering signal is detected during shock wave therapy. The resonant acoustic scattering signal is indicative of internal stress vibrations in the kidney stone, where the internal stress vibrations are in response to shock waves impacting the kidney stone. The resonant acoustic scattering signal is processed to determine a frequency spectrum of the stress vibrations, which is monitored during therapy in order to determine if the kidney stone is fragmented. A change in the frequency spectrum is indicative of fragmentation.

In at least one exemplary embodiment of such a method, the step of processing the resonant acoustic scattering signal to determine a frequency spectrum of the stress vibrations comprises the steps of determining and recording a frequency spectrum induced by an initial shock wave, and determining and recording a frequency spectrum induced by subsequent shock waves. The step of monitoring the frequency spectrum of the stress vibration during therapy in order to determine when the kidney stone is fragmented comprises the step of dividing the frequency spectrum of subsequent shock waves by the frequency spectrum of the first shock wave to determine a frequency ratio indicative of a change in size of the kidney stone. A frequency ratio greater than about two is indicative that the kidney stone has fragmented. Initial fracture can be readily identified from a time domain and a frequency domain analysis.

In yet another exemplary embodiment of such a method, the frequency spectrum is monitored to determine when a frequency of the stress vibrations is greater than or substantially equal to a value indicative of a substantially comminuted kidney stone. The frequency corresponding to substantial comminution is a function of the size of the stone fragments after comminution (clinicians generally aim for fragments ranging from about 1 mm to about 3 mm in size), and the speed of sound in the kidney stone and its fragments. In at least one exemplary embodiment, it is assumed that the frequency corresponding to substantial comminution is about 750 kHz. Kidney stone size can be readily identified from a frequency domain analysis, and less so, from a time domain analysis.

Various different types of acoustic detectors can be used to acquire the resonant acoustic scattering signal, including (but not limited to) a detector that is confocal to a source of the shock waves, a broadband detector, a narrow band detector, and a plurality of detectors. In at least one exemplary embodiment, the detectors are expected to be disposable.

In at least one exemplary embodiment of such a method, the step of processing the resonant acoustic scattering signal to determine a frequency spectrum of the stress vibrations comprises the steps of filtering the resonant acoustic scattering signal with a high pass filter to remove transient low frequency artifacts caused by the source of the shock waves, and de-convolving the filtered acoustic signal to remove artifacts induced by the filter.

In yet another exemplary embodiment of such a method, the method further comprises the step of using an acoustic pressure wave of a known magnitude to determine a degree of the fragmentation of the kidney stone, by irradiating the kidney stone fragments with an acoustic pressure wave of a known magnitude, and determining a displacement of the kidney stone fragments induced by the acoustic pressure wave. A magnitude of the displacement is a function of the size of the kidney stone fragments, with relatively larger fragments experiencing relatively smaller displacements. Several transducer configurations can be employed, including using a transducer that is disposed along a shock wave axis of the shock waves used in the therapy, or using a transducer that is disposed at an angle relative to a shock wave axis of the shock waves used in the therapy, and disposed outside of an acoustic path of the shock waves. Doppler ultrasound can be used to implement the displacement based techniques.

Acoustic pressure waves cause fragmented kidney stone particles to disperse, enabling such particles to be more readily distinguished from an intact kidney stone in fluoroscopic or ultrasound images, and to facilitate removal of the fragments from the kidney. Such acoustic pressure waves are less energetic than the shock waves and will not alone cause fragmentation. Furthermore, such displacement data and dispersion of fragments can be used to determine when the kidney stone has fragmented, because displacement data for an intact stone will be different (smaller) than displacement data for kidney stone fragments, and the dispersal will facilitate visualizing the dispersed fragments in an ultrasound or fluoroscopic images (the dispersed fragments are easier to identify, but tightly packed fragments are hard to distinguish from intact kidney stones).

A related system includes a shock wave source, a receiver configured to detect the resonant acoustic scattering wave, and means to process the resonant acoustic scattering signal and determine at least one of when the kidney stone has fragmented and whether substantial comminution has been achieved.

A second aspect of the novel concepts disclosed herein is directed to a method for determining an endpoint in shock wave therapy of a kidney stone. In such a method, imaging ultrasound is used to determine a degree of the fragmentation of the kidney stone, by irradiating the kidney stone fragments with an acoustic pressure wave of known magnitude, and determining a displacement of the kidney stone fragments induced by the acoustic pressure wave. A magnitude of the displacement is a function of the size of the kidney stone fragments, with relatively larger fragments experiencing relatively smaller displacements. Such displacement measurements will enable a mass of relatively closely spaced kidney stone particles to be easily differentiated from an intact kidney stone. Empirical displacement data can be correlated with fragments of specific size, such that displacement data obtained during therapy can provide an indication of particle size.

Acoustic pressure waves cause fragmented kidney stones particles to disperse, facilitating removal of the fragments from the kidney. Such acoustic pressure waves are less energetic than the shock waves, and will not alone cause fragmentation.

A related system includes a shock wave source and means to acquire displacement data and determine when the displacement data indicates that substantial comminution has been achieved.

A third aspect of the novel concepts disclosed herein is directed to yet another method for determining when an endpoint in shock wave therapy of a kidney stone has been reached. The method includes the steps of detecting a resonant acoustic scattering signal during therapy, since the resonant acoustic scattering signal is indicative of internal stress vibrations in the kidney stone. The resonant acoustic scattering signal is processed to determine a frequency spectrum of the stress vibrations, and the frequency spectrum of the stress vibration is monitored during the therapy in order to determine when a frequency of the stress vibrations is greater than or substantially equal to about 750 kHz. Such a frequency is indicative that the kidney stone is substantially comminuted, and that the endpoint of the shock wave therapy has been reached. The 750 kHz value is an estimated value that can be used generally, but is not intended to be limiting on this approach. More accurate values can be determined by defining the final particle size desired (e.g., 1 mm, 2 mm, 3 mm, or 4 mm), and by calculating the corresponding resonant acoustic scattering frequency as a function of particle size and the speed of sound in a specific kidney stone (where the speed has been empirically determined), or the speed of sound in kidney stones of the same type. If desired, the displacement based endpoint and the resonant acoustic scattering endpoint can be used during the same therapy.

In at least one exemplary embodiment of such a method, the step of processing the resonant acoustic scattering signal to determine a frequency of the stress vibrations includes the steps of filtering the resonant acoustic scattering signal with a high pass filter to remove transient low frequency artifacts caused by the source of the shock waves, and de-convolving the filtered acoustic signal to remove artifacts induced by the filter.

A related system includes a shock wave source and means to acquire resonant acoustic scattering frequency data and determine when the frequency data indicates that substantial comminution has been achieved.

A fourth aspect of the concepts disclosed herein is directed to a system and method for reducing a dose delivered to a patient during shock wave therapy. The method includes at least one step selected from a group consisting of monitoring a resonant acoustic scattering frequency spectrum to determine when the kidney stone has fragmented and if a remaining dose will be sufficient to substantially comminute the kidney stone. A resonant acoustic scattering frequency spectrum is monitored to determine if the frequency spectrum corresponding to substantial comminution of the kidney stone has been reached. Displacement data are monitored during therapy to determine when the kidney stone has fragmented and if the remaining dose will be sufficient to substantially comminute the kidney stone. The displacement data are monitored during therapy to determine if the displacement data correspond to substantial comminution of the kidney stone. Using a pressure pulse to disperse kidney stone fragments, such fragments can be made more visible in an image, to determine when the kidney stone has fragmented and if the remaining dose will be sufficient to substantially comminute the kidney stone. The system includes a shock wave source for administering shock waves, and means to implement the steps generally consistent with the corresponding method.

With respect to the step of monitoring the frequency spectrum of the internal stress vibrations of the kidney stone to determine when the kidney stone has fragmented, this technique can reduce the dose delivered to the patient during shock wave therapy by determining when the kidney stone has fragmented. Accordingly, if fragmentation has occurred relatively late in the shock wave therapy, and it is unlikely that a remaining portion of a maximum allowed dose will result in the kidney stone being substantially comminuted, then the shock wave therapy can be terminated. This technique thereby can reduce the dose delivered to the patient during shock wave therapy, by not delivering shock waves that are unlikely to be effective in substantially comminuting the kidney stone.

By monitoring the frequency spectrum of the internal stress vibrations of the kidney stone to determine when a frequency of the internal stress vibrations of the kidney stone substantially corresponds to about 750 kHz, the doses delivered to the patient during shock wave therapy are reduced, because no more shock waves than are required to substantially comminute the kidney stone are administered. As discussed in greater detail below, 750 kHz represents a reasonable approximation of the desired frequency; however, a more precise value can be determined if the speed of sound in a particular kidney stone is known.

It should be recognized that such a method encompasses the various combinations and permutations of the individual method steps, including embodiments where only a single one of the steps is implemented, or where only two of the steps are implemented.

A fifth aspect of the novel concepts disclosed herein relates to kits for use with a system for providing shock wave therapy to comminute a kidney stone. Such kits will enable the concepts disclosed herein to be incorporated into existing lithotripter systems. In at least some exemplary embodiments, the kits include instructions. The kits can include either machine executable instructions to be implemented on a processor in the existing shock therapy system, or a controller configured to implement steps defined by the kit.

A first exemplary kit includes means to detect a resonant acoustic scattering signal during therapy, the resonant acoustic scattering signal being indicative of internal stress vibrations in the kidney stone, where the internal stress vibrations are in response to shock waves impacting the kidney stone, means to measure a displacement of the kidney stone induced by the pressure pulse of known amplitude, and means to analyze the resonant acoustic scattering signal during therapy to determine whether the kidney stone has fragmented, and/or whether the kidney stone is substantially comminuted.

A second exemplary kit includes means to direct a pressure pulse of known amplitude toward the kidney stone, means to measure a displacement of the kidney stone induced by the pressure pulse of known amplitude, and means to analyze the measured displacement to determine whether the kidney stone has fragmented and/or whether the kidney stone is substantially comminuted.

Yet another exemplary kit includes an acoustic receiver configured to detect a resonant acoustic scattering signal during therapy and to logically couple with an existing system input, and software to program the controller to execute desired functions. The resonant acoustic scattering signal is indicative of internal stress vibrations in the kidney stone, where the internal stress vibrations are in response to shock waves impacting the kidney stone. The software (i.e., a memory medium on which are stored machine executable instructions) enables the system to carry out the step of processing the resonant acoustic scattering signal to determine a frequency spectrum of the stress vibrations, and monitoring the frequency spectrum of the stress vibrations during therapy in order to determine if the kidney stone is fragmented.

In one exemplary embodiment of such a kit, the software enables the system to carry out the steps of determining and recording a frequency spectrum induced by an initial shock wave, and determining and recording a frequency spectrum induced by subsequent shock waves. The frequency spectrum of subsequent shock waves is then divided by the frequency spectrum of the first shock wave to determine a frequency ratio. A frequency ratio greater than about two is indicative that the kidney stone has fragmented.

In another exemplary embodiment of such a kit, the software enables the system to carry out the steps of monitoring the frequency spectrum to determine when a frequency of the stress vibrations substantially corresponds to about 750 kHz (which is a frequency generally indicative that the kidney stone is substantially comminuted).

A sixth aspect of the novel concepts disclosed herein encompasses a system and method for a providing an indication of when a kidney stone is fragmented during shock wave therapy. The method comprises at least one step selected from the group consisting essentially of the following steps. A first step provides for using an acoustic pressure pulse to determine when the kidney stone has fragmented, by irradiating the kidney stone with an acoustic pressure pulse of known magnitude, and determining a displacement of the kidney stone induced by the acoustic pressure pulse. In this step, a magnitude of the displacement is a function of the size of the kidney stone, and fragmentation is indicated by the displacement data, because a relatively larger intact kidney stone will have a relatively smaller displacement than will relatively smaller kidney stone fragments. In a second step, a resonant acoustic scattering frequency spectrum is measured to determine when the kidney stone has fragmented. By monitoring the resonant acoustic scattering frequency spectrum during the shock wave therapy, an increase in the resonant acoustic scattering frequency can be detected, which is indicative of fragmentation of the kidney stone.

The system includes a shock wave source, and at least one element selected from a group consisting essentially of: (1) means to provide the indication of when the kidney stone is fragmented based on monitoring a resonant acoustic scattering signal during therapy; and, (2) means to provide the indication of when the kidney stone is fragmented based on monitoring a displacement of the kidney stone induced by an acoustic pressure pulse applied at various times during the therapy.

A seventh aspect of the novel concepts disclosed herein encompasses a system and method for treating a kidney stone using shock waves gated with vibro-acoustography. The method includes the step of using vibro-acoustography to gate a delivery of a shock wave, thereby minimizing a number of shock waves that are delivered but miss the kidney stone. During therapy, at least one additional step is performed that is selected from a group consisting of monitoring a frequency spectrum indicative of internal stress vibrations in the kidney stone during the shock wave therapy, to determine when the kidney stone has fragmented; monitoring a frequency spectrum indicative of internal stress vibrations in the kidney stone during the shock wave therapy, to determine when the frequency spectrum substantially corresponds to substantially comminuted kidney stone fragments; using an acoustic pressure pulse to determine when the kidney stone has fragmented, by irradiating the kidney stone with an acoustic pressure pulse of known magnitude; and, determining a displacement of the kidney stone induced by the acoustic pressure pulse. A magnitude of the displacement is a function of the size of the kidney stone, and fragmentation is indicated by the displacement data, because a relatively larger intact kidney stone will have a relatively smaller displacement than will relatively smaller kidney stone fragments. The group also includes using the acoustic pressure pulse to disperse kidney stone fragments, thereby enabling imaging modalities to more clearly differentiate fragmented kidney stones from intact kidney stones; and, using an acoustic pressure pulse to determine that the kidney stone is substantially comminuted, by irradiating the kidney stone fragments with an acoustic pressure pulse of known magnitude, determining a displacement of the kidney stone fragments induced by the acoustic pressure pulse.

The system includes a shock wave source, means to use vibro-acoustography to gate a delivery of a shock wave, thereby minimizing a number of shock waves that are delivered but miss the kidney stone; and at least one element selected from a group consisting essentially of means to provide an indication of when the kidney stone is substantially comminuted based on monitoring a resonant acoustic scattering signal during therapy; means to provide an indication of when the kidney stone is substantially comminuted based on monitoring a displacement of the kidney stone induced by an acoustic pressure pulse applied at various times during the therapy; means to provide an indication of when the kidney stone is fragmented based on monitoring a resonant acoustic scattering signal during therapy; means to provide an indication of when the kidney stone is fragmented based on monitoring a displacement of the kidney stone induced by an acoustic pressure pulse applied at various times during the therapy; and, means to apply an acoustic pressure pulse to disperse kidney stone fragments. This dispersal is carried out by performing at least one function selected from a group consisting of enabling imaging modalities to more clearly differentiate fragmented kidney stones from intact kidney stones, and facilitating removing the kidney stone fragments from the kidney.

An eighth aspect of the novel concepts disclosed herein encompasses a system and method for treating a kidney stone using shock waves and an acoustic pressure pulse. The method includes at least one of the steps of using the acoustic pressure pulse to determine when the kidney stone has fragmented, by irradiating the kidney stone with an acoustic pressure pulse of known magnitude, and determining a displacement of the kidney stone induced by the acoustic pressure pulse. A magnitude of the displacement being a function of the size of the kidney stone, and fragmentation is indicated by the displacement data because a relatively larger intact kidney stone will have a relatively smaller displacement than will relatively smaller kidney stone fragments. The method also includes the step of using the acoustic pressure pulse to disperse kidney stone fragments, thereby enabling imaging modalities to more clearly differentiate fragmented kidney stones from intact kidney stones. Another step is using the acoustic pressure pulse to determine that the kidney stone is substantially comminuted, by irradiating the kidney stone fragments with an acoustic pressure pulse of known magnitude, determining a displacement of the kidney stone fragments induced by the acoustic pressure pulse, a magnitude of the displacement being a function of the size of the kidney stone fragments, with relatively larger fragments experiencing relatively smaller displacements, and determining when the measured displacement is indicative of substantially comminuted kidney stone fragments. The system includes a shock wave source and at least one means to implement at least one of the method steps described above.

A ninth aspect of the novel concepts disclosed herein encompasses an acoustic receiver configured to detect a resonant acoustic scattering signal during shock wave therapy of a kidney stone, the resonant acoustic scattering signal being indicative of internal stress vibrations in the kidney stone, where the internal stress vibrations are in response to shock waves impacting the kidney stone, the acoustic receiver comprising a piezoelectric sensor stretched into a spherical curvature to heighten a sensitivity of the receiver to scattering from a center of the radius of curvature. In at least one exemplary embodiment the acoustic receiver includes a pre-amplifier and a high pass filter.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein:

FIGS. 1A-1D schematically illustrate how a shock wave induces a resonant acoustic scattering wave during shock wave therapy of a kidney stone, the resonant acoustic scattering wave being capable of being detected by an acoustic receiver spaced apart from the kidney stone;

FIG. 2 schematically illustrates collecting a resonant acoustic scattering signal during shock wave therapy of a kidney stone, in an exemplary technique employed in several aspects of the concepts noted above and disclosed herein;

Figure 4:
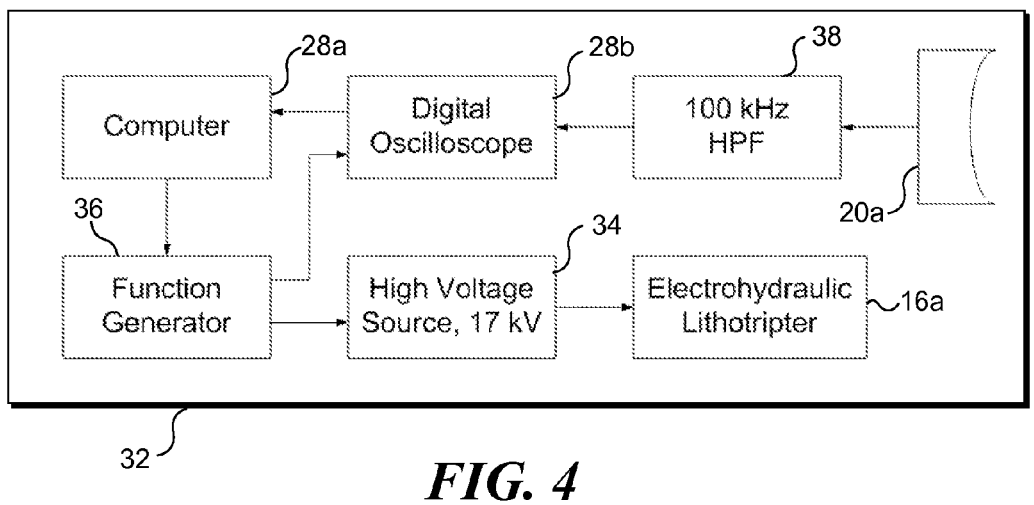
FIG. 4 is a functional block diagram illustrating an empirical system for collecting a resonant acoustic scattering signal during shock wave therapy of a kidney stone, the empirical system having been used to collect data as disclosed herein.
Figure 10:
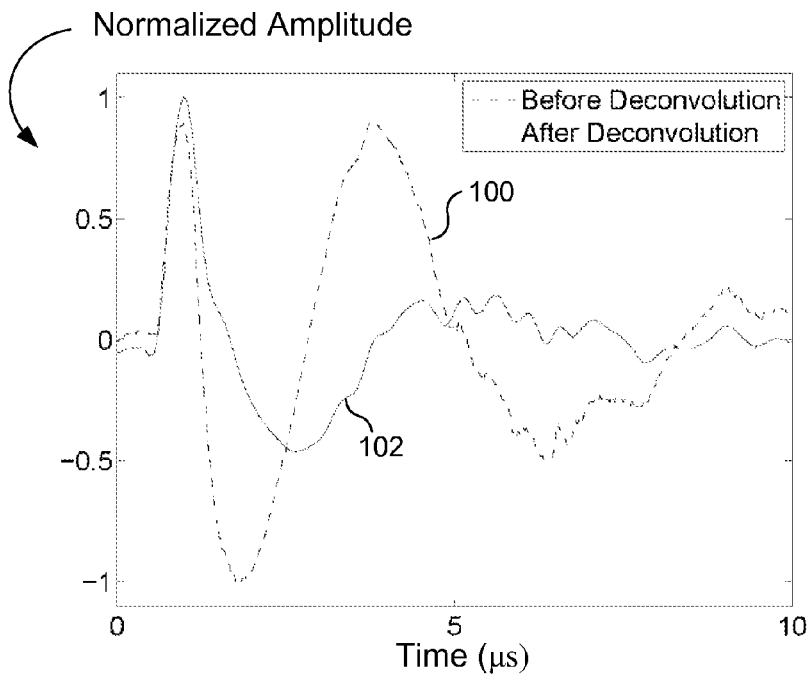
Figure 11A:
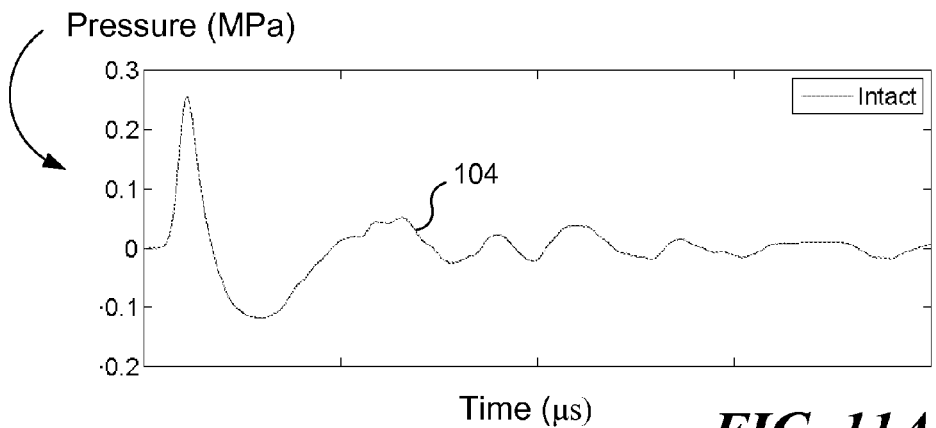
Figure 11B:
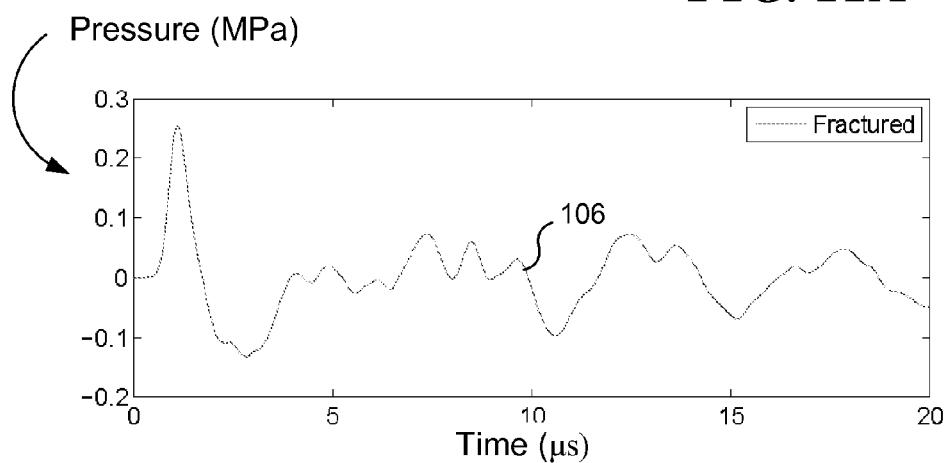
Figure 12C:
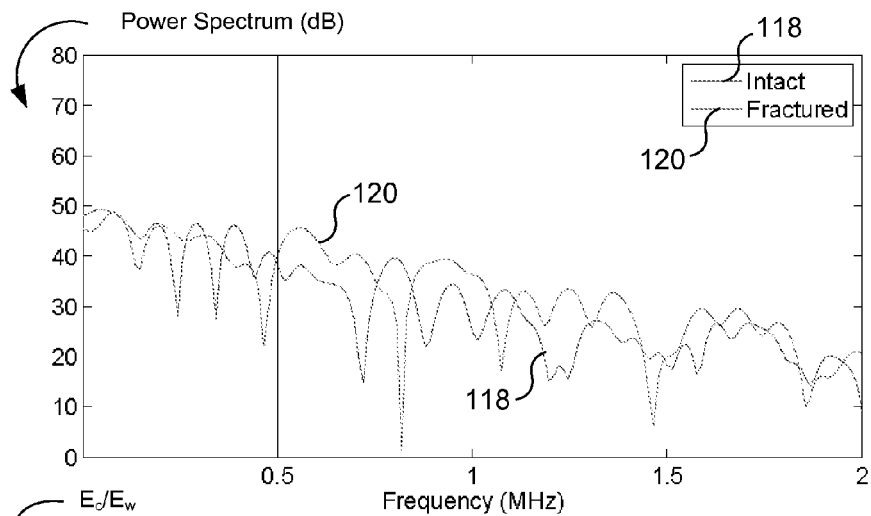
Figure 12D:
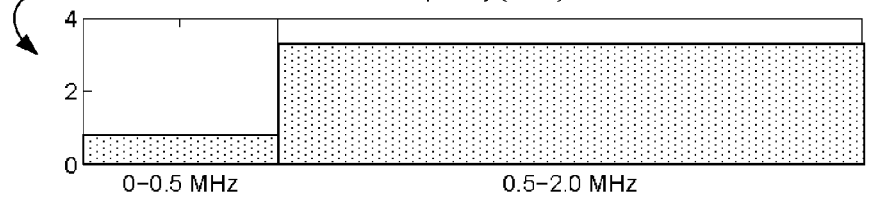
Figure 13:
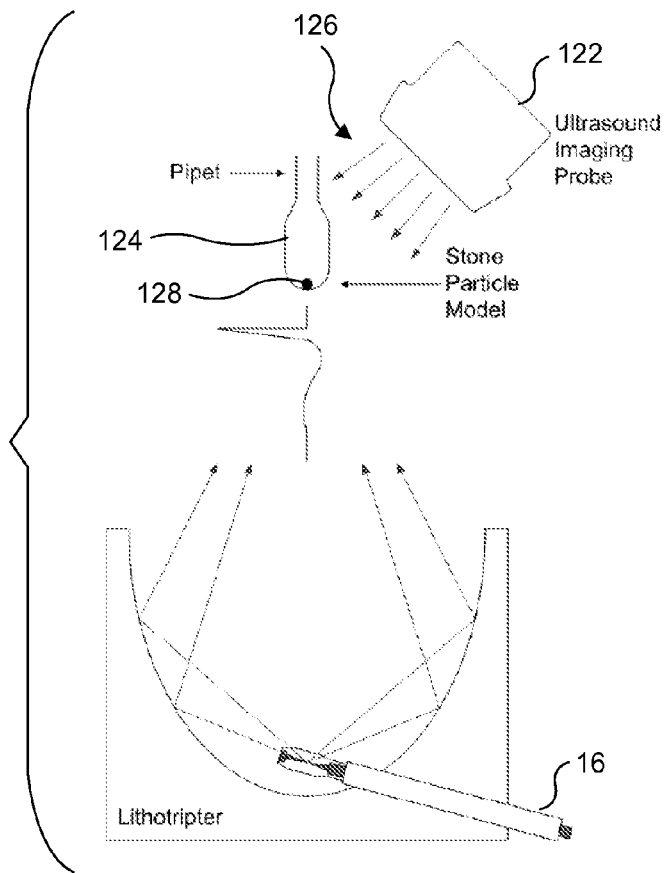
Figure 14A:
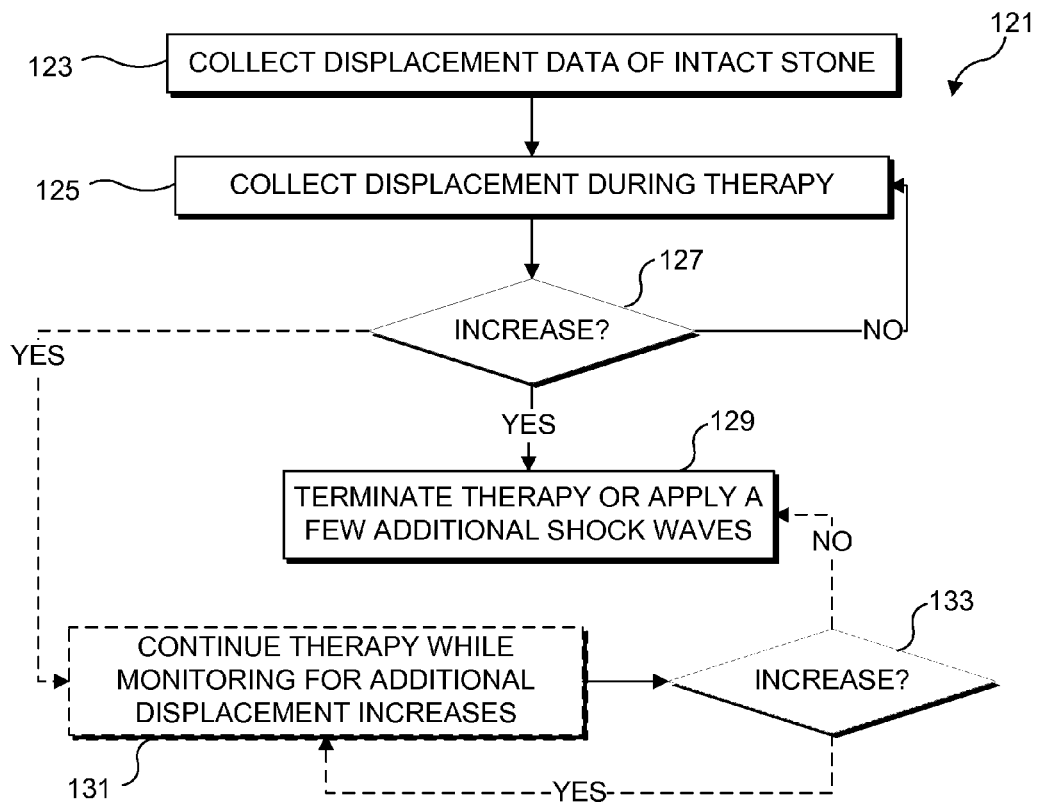
Figure 14B:
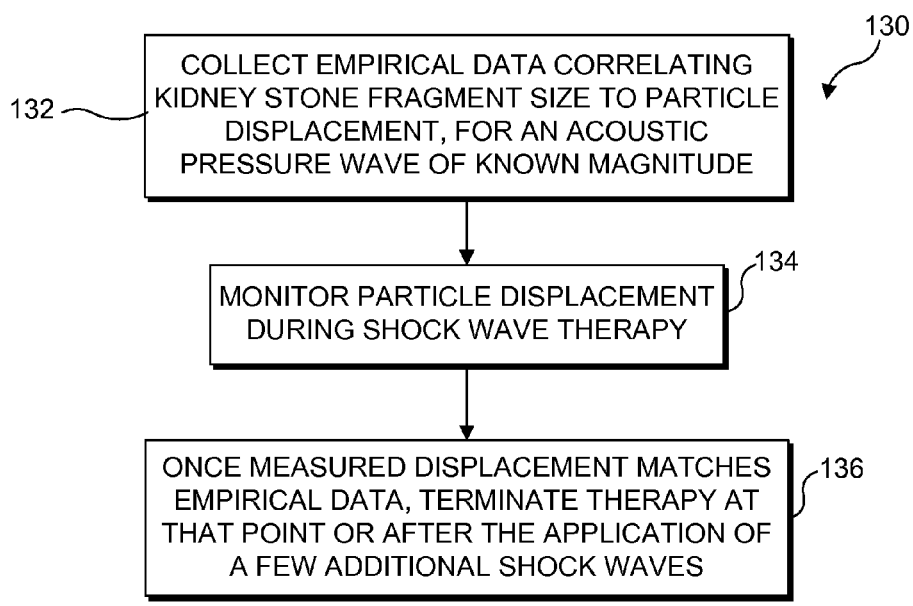
Figure 15:
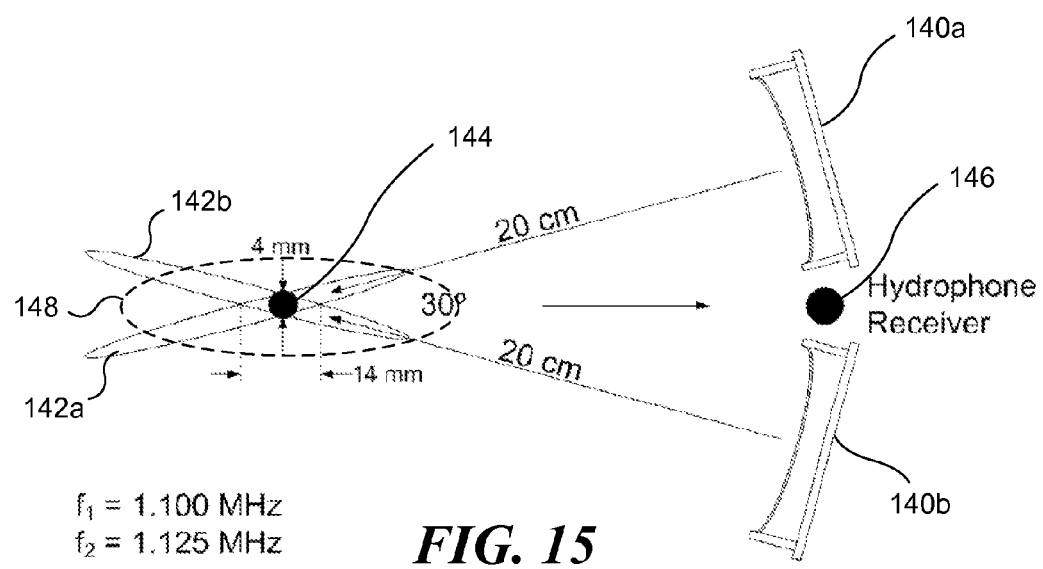
Figure 16A:
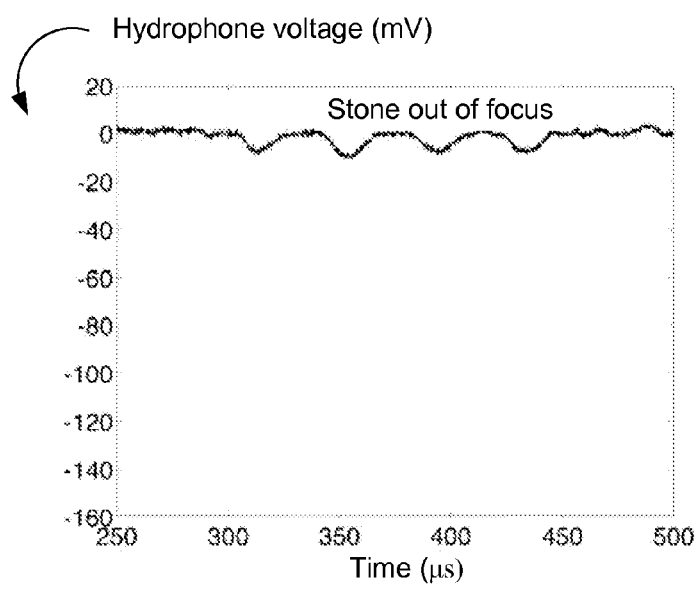

FIG. 10 graphically illustrates a de-convolution of a resonant acoustic scattering signal acquired by the empirical system of FIG. 4 and a simulated kidney stone, the de-convolution correcting an artifact induced by the high pass filter;

FIG. 11A graphically illustrates a pressure versus time curve based on a resonant acoustic scattering signal of an intact simulated kidney stone, the resonant acoustic scattering signal having been theoretically calculated;

FIG. 11B graphically illustrates a pressure versus time curve based on a resonant acoustic scattering signal of a fractured simulated kidney stone, the resonant acoustic scattering signal having been theoretically calculated;

FIG. 11C graphically illustrates a power versus frequency curve based on a resonant acoustic scattering signal of both an intact simulated kidney stone and a fractured kidney stone, the resonant acoustic scattering signal having been theoretically calculated;

FIG. 11D graphically illustrates a frequency ratio based on resonant acoustic scattering signals having been theoretically calculated, illustrating how the ratio is indicative of the point at which a simulated kidney stone fractures;

FIG. 12A graphically illustrates a voltage versus time curve based on a resonant acoustic scattering signal of an intact simulated kidney stone, the resonant acoustic scattering signal having been acquired by the empirical system of FIG. 4;

FIG. 12B graphically illustrates a voltage versus time curve based on a resonant acoustic scattering signal of a fractured simulated kidney stone, the resonant acoustic scattering signal having been acquired by the empirical system of FIG. 4;

FIG. 12C graphically illustrates a power versus frequency curve based on a resonant acoustic scattering signal of both an intact simulated kidney stone and a fractured kidney stone, the resonant acoustic scattering signal having been acquired by the empirical system of FIG. 4;

FIG. 12D graphically illustrates a frequency ratio based on resonant acoustic scattering signals acquired by the empirical system of FIG. 4, illustrating how the ratio is indicative of the point at which a simulated kidney stone fractures;

FIG. 13 schematically illustrates an empirical system employed to correlate a displacement of simulated kidney stone fragments induced by a pressure pulse of a known magnitude for a particular particle size, to develop a displacement based endpoint for terminating shock wave therapy;

FIG. 14A is a flow chart of exemplary steps using displacement data collected during shock wave therapy of a kidney stone to determine whether the kidney stone has been fragmented, enabling a first displacement based metric for shock wave therapy to be achieved;

FIG. 14B is a flowchart illustrating exemplary steps for correlating a displacement of simulated kidney stone fragments induced by a pressure pulse of a known magnitude for a particular particle size, to develop a second displacement based metric for shock wave therapy;

FIG. 15 schematically illustrates an empirical system employed to reduce a dose required to comminute kidney stones by using vibro-acoustography to trigger the application of a shock wave, thereby reducing the number of shock waves that miss the kidney stone;

FIG. 16A graphically illustrates a voltage versus time curve detected by the hydrophone in FIG. 15 when a simulated kidney stone was not within the overlapping foci of the shock waves;

FIG. 16B graphically illustrates a voltage versus time curve detected by the hydrophone in FIG. 15 when a simulated kidney stone was within the overlapping foci of the shock waves;

FIG. 17 is a flow chart of exemplary steps for reducing a dose required to comminute kidney stones by using vibro-acoustography to trigger the application of a shock wave, thereby reducing an amount of shock waves that miss the kidney stone; and FIG. 18 shows the table of material properties used to generate the synthetic data employed in the graphs of FIGS. 11A and 11B.

DESCRIPTION

Figures and Disclosed Embodiments are not Limiting

Exemplary embodiments are illustrated in referenced Figures of the drawings. It is intended that the embodiments and Figures disclosed herein are to be considered illustrative rather than restrictive. No limitation on the scope of the technology and of the claims that follow is to be imputed to the examples shown in the drawings and discussed herein.

FIGS. 1A-1D schematically illustrate how a shock wave induces a resonant acoustic scattering wave during shock wave therapy of a kidney stone, the resonant acoustic scattering wave being detectable by an acoustic receiver spaced apart from the kidney stone. These Figures are based on shadow graphic observations of a lithotripter shock wave scattering from a stone. The original images on which these Figures are based can be found in provisional patent application Ser. No. 60/829,510 (filed on Oct. 13, 2006, in which the present application claims priority). The original grayscale images have not been provided herein because they are poorly suited for reproduction. The original images were captured in water with a high-speed camera moments after the shock wave emission (each Figure indicates the elapsed time after the generation of the shock wave), showing the interaction between the shock wave and a simulated kidney stone. The simulated kidney stone was cylindrical in shape (6.5 mm in diameter and 8.5 mm in length) and was made from low expansion gypsum cement (Ultracal-30™). This gypsum based material is chemically very similar to actual kidney stones and is well accepted as a reasonable kidney stone equivalent.

Figures 1A, 1B, 1C, 1D:
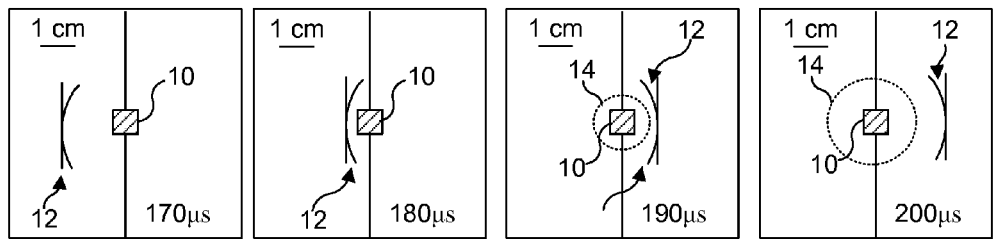

In FIG. 1A (based on an image captured 170 μs after the shock wave was generated), a shock wave 12 (moving left to right) has not yet impacted a simulated kidney stone 10. In FIG. 1B (based on an image captured 180 μs after the shock wave was generated), shock wave 12 (moving left to right) is just about to impact simulated kidney stone 10. In FIG. 1C (based on an image captured 190 μs after the shock wave was generated), shock wave 12 (moving left to right) has already impacted simulated kidney stone 10 and is moving past the simulated kidney stone. A resonant acoustic scattering wave 14 has been generated by internal stress vibrations within the simulated kidney stone and is propagating outwardly and away from the simulated kidney stone. In FIG. 1D (based on an image captured 200 μs after the shock wave was generated), shock wave 12 (moving left to right) has moved significantly beyond the simulated kidney stone, and resonant acoustic scattering wave 14 has moved further away from the simulated kidney stone.

The concepts disclosed herein are based on the recognition of several important properties about the resonant acoustic scattering wave shown in FIGS. 1C and 1D. Significantly, the internal stress vibrations and the resulting resonant acoustic scattering waves are directly caused by the shock wave impacting upon the simulated kidney stone. The term "resonant acoustic scattering wave" (as used herein and in the claims that follow) has been selected to indicate an acoustic wave (i.e., acoustic radiation) generated as a result of internal stress vibrations in a kidney stone or a simulated kidney stone, where the internal stress vibrations have been induced by a shock wave impacting on the kidney stone. In other words, "resonant acoustic scattering" is a term used to describe acoustic radiation caused by reverberations within a stone struck by a shock wave. It should be recognized that the resonant acoustic scattering wave is generated well before any cavitational effects are induced by the shock wave, such that detecting the resonant acoustic scattering wave is not equivalent to detecting acoustical waves corresponding to cavitation. Thus, while resonant acoustic scattering waves and acoustic waves generated by cavitation each represent a different type of acoustical wave, the two are not equivalent.

Another significant characteristic of resonant acoustic scattering waves is that internal stress vibrations for a relatively smaller stone will generate distinguishably different resonant acoustic scattering waves than internal stress vibrations for a relatively larger stone. This result is because the dimensions of the stones are different. An internal stress wave in a relatively larger stone must traverse a relatively longer distance than an internal stress wave in a relatively smaller stone. Because of this difference in the distance traversed, which relates to resonant wavelength, the frequency of a resonant acoustic scattering wave from a relatively small stone is higher than the frequency of a resonant acoustic scattering wave from a relatively larger stone. An analogous concept relates to differentiating the size of a bell based on its pitch (smaller bells have a higher pitch).

When an intact kidney stone begins to fracture, the fracture will affect the internal stress vibrations by changing a length of a path of the internal stress vibrations in the stone. The change in the internal stress vibration path will in turn, affect the resonant acoustic scattering wave. As the stone becomes more and more fragmented during shock wave therapy, a plurality of relatively small size fragments will be created. The resonant acoustic scattering wave for each of these relatively smaller size stones will be markedly distinguishable from the resonant acoustic scattering wave for a relatively larger intact stone. In fact, as will be described in greater detail below, stones of a particular size correlate very well to a particular frequency of the resonant acoustic scattering wave. Thus, the frequency spectrum of the resonant acoustic scattering wave can be used to determine the size of the kidney stone fragments.

Figure 2:
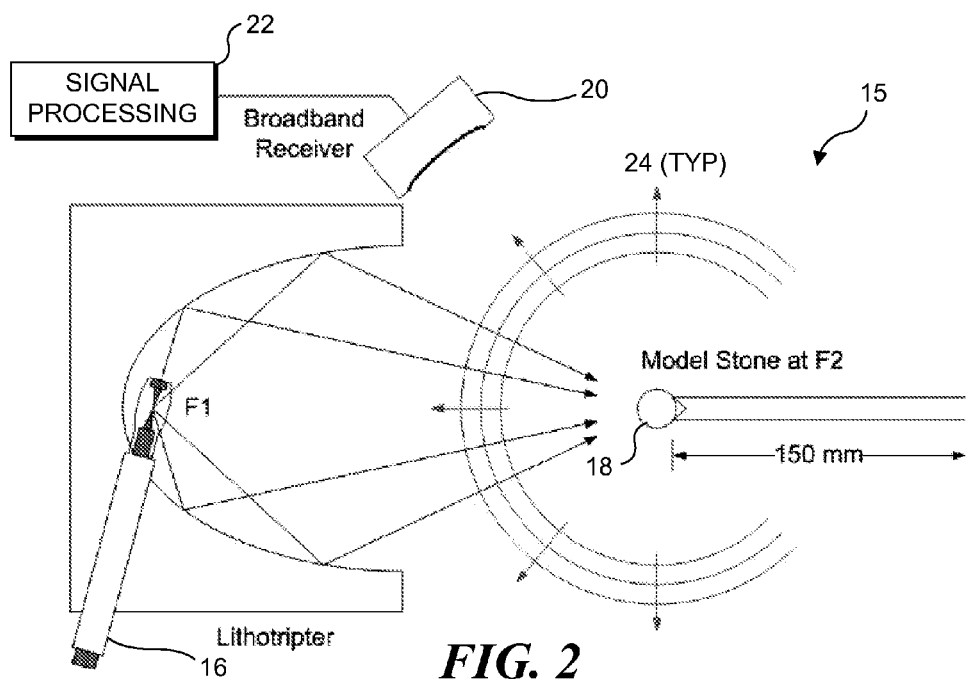

FIG. 2 schematically illustrates a system 15 being used for collecting a resonant acoustic scattering signal during shock wave therapy of a kidney stone. As shown in FIG. 2, system 15 includes a shock wave source 16 (i.e., a lithotripter), a kidney stone 18 generally disposed at a focal point of the shock wave source, an acoustical receiver 20, and a signal processing component 22. When the shock wave source is triggered, the shock wave propagates towards the kidney stone. As described above, internal stress vibrations are generated within the kidney stone when the shock wave impacts the kidney stone. A resonant acoustic scattering wave 24 propagates outwardly and away from kidney stone 18. The acoustical receiver detects the resonant acoustic scattering wave and produces a signal indicative of the resonant acoustic scattering wave. That signal is processed by signal processing component 22, to provide a frequency spectrum that can be used to evaluate a degree to which the kidney stone has been fragmented.

Significantly, acoustical receiver 20 can be positioned at a location that is spaced apart from the kidney stone, so long as an acceptably effective transmission medium is between the kidney stone and the receiver. This requirement means that the acoustical receiver can be positioned externally of the patient (such that tissue acts as the transmission medium).

While exemplary receivers will be described in greater detail below, it should be recognized that many different acoustical receivers can be employed, so long as the acoustical receiver that is used is able to detect the resonant acoustic scattering wave described above. FIG. 2 indicates that the acoustic receiver is a broadband receiver. Such an implementation is intended to be exemplary, rather than limiting. One or more narrowband acoustic receivers can also be employed, so long as the receivers being used are actually capable of receiving the resonant acoustic scattering wave. In general, conventional ultrasound imaging transducers are capable of both generating and receiving acoustical waves. In theory, an ultrasound imaging transducer could be used to detect the resonant acoustic scattering wave. Particularly because many shock wave therapy systems include ultrasound imaging components, a single transducer might theoretically be used to both acquire the resonant acoustic scattering signal and to provide ultrasound imaging capability. As a practical matter, modifying control circuitry for an ultrasound imaging system to enable an ultrasound transducer to be used to receive a resonant acoustic scattering wave may be more costly and technically challenging than simply employing a separate acoustical receiver specifically configured to receive the resonant acoustic scattering wave. For example, one exemplary system that implements the concepts disclosed herein can employ a plurality of disposable resonant acoustic scattering wave receivers, which can be used once with a single patient and then discarded (much in the way disposable EKG sensors are employed).

With respect to using existing ultrasound imagers, other than providing a controller configured to manipulate the resonant acoustic scattering signal as discussed below, it is possible that few modifications would be needed. Most ultrasound imagers are made for use at frequencies ranging from about 1 MHz-10 MHz. Ultrasound imaging transducers are generally made as broadband as possible. It is believed that receivers configured to detect resonant acoustic scattering waves should be able to detect frequencies ranging from about 300-800 kHz, or as high as 1000 kHz. It is reasonable to expect that that existing 1 MHz ultrasound transducers would be usable for receiving the resonant acoustic waves, especially for detecting such waves at a threshold frequency of about 750 kHz. In general, the resonant acoustic scattering wave intensity is relatively strong, so even if imaging probes are considered to have a bandwidth slightly higher that the target frequency of about 750 kHz, transducers used in available imaging probes certainly should be capable of detecting such a relatively strong resonant acoustic scattering wave. For commercial systems, manufacturers may want to provide ultrasound imaging transducers designed for lower frequencies, or provide systems that incorporate a low frequency element in an array of transducers. With respect to detecting the resonant acoustic scattering wave, ultrasound imaging transducers are actually more complex than what is required. For example, many ultrasound imagers include 128 elements, which is substantially more than the one (or several) required to detect the resonant acoustic scattering wave. In the empirical studies regarding resonant acoustic scattering disclosed herein, a relatively broadband receiver was employed, to generate as much data as possible to learn about the resonant acoustic scattering phenomena. Having identified the more important frequencies, it is evident that a narrowband receiver could instead be employed. If a broader band signal is desired, it is possible to measure the frequency response of the transducer and then de-convolve that with the measured signal to correct for the bias of the receiver. This step can be used to make a non-flat (i.e., narrowband) frequency response flatter (i.e., more broadband).

Figure 3:
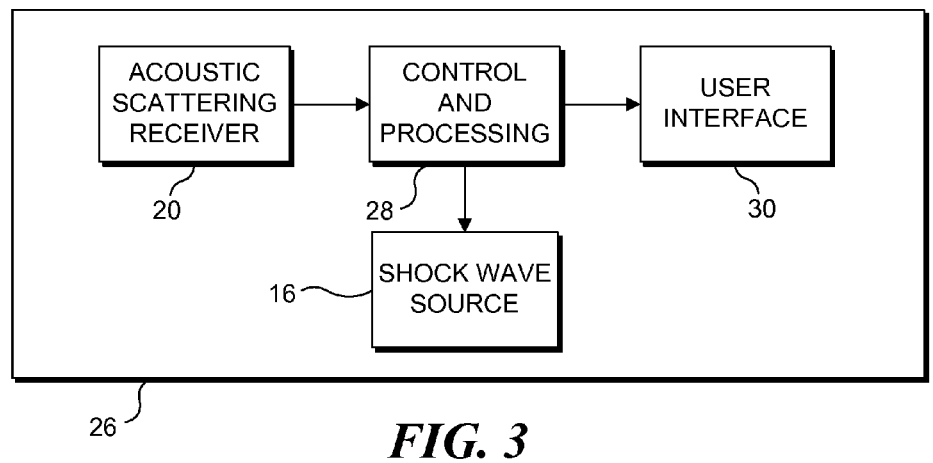
FIG. 3 is a functional block diagram illustrating one exemplary system for collecting a resonant acoustic scattering signal during shock wave therapy of a kidney stone.

FIG. 3 is a functional block diagram illustrating one exemplary system 26 for collecting a resonant acoustic scattering signal during shock wave therapy of a kidney stone. System 26 includes shock wave source 16, resonant acoustic scattering receiver 20, a control and processing component 28, and a user interface 30 (generally a display, although it should be recognized that other types of user interfaces, such as audible outputs, can also be beneficially employed). A computer represents an exemplary control and processing component, although it should be recognized that other types of logical processing components can also be employed, such as custom logic circuits and application-specific integrated circuits (ASICs).

FIG. 4 is a functional block diagram illustrating an empirical system 32 that was utilized to collect resonant acoustic scattering waves generated by applying shock waves to simulated kidney stones. System 32 incorporated an electro-hydraulic lithotripter 16a, a high voltage source 34 (for energizing the lithotripter), a customized resonant acoustic scattering wave receiver 20a, a high pass filter 38 (utilized to remove noise from the high voltage source), a digital oscilloscope 28b (used for performing a de-convolution step to remove signal artifacts produced by the high pass filter), a function generator 36 (used to trigger the high voltage source and control the oscilloscope), and a computer 28a (used to control the function generator and process the de-convolved signal from the oscilloscope).

In experimental studies conducted using system 32 (described in greater detail below), intact and fractured stone models were placed individually in a water tank filled with de-gassed water, at the focus of electro-hydraulic lithotripter (a research electro-hydraulic lithotripter patterned after the Dornier HM3™). The stones were subjected to 20 shock waves. Each shock wave was generated with a lithotripter charging potential of 17 kV, corresponding to a 25 MPa peak positive pressure and a 10 MPa peak negative pressure.

In some studies the stones were modeled using glass, while later studies employed stones made from gypsum based cement. In one study, the intact stone was modeled using a glass sphere of 5 mm radius that was bonded with epoxy to a counter-sunk aluminum rod for rigid placement in the acoustic field. In a related study, a fractured stone was modeled with two glass hemispheres of 5 mm radius that were bonded together with a 1 mm film of epoxy, which was smaller in size than the hemispheres, such that a fracture existed in the combined stone along the adhesive layer. Resonant acoustic scatter from each shock wave was measured with resonant acoustic scattering wave receiver 20a (a focused receiver described in greater detail below). The resulting signal was filtered at 100 kHz using high pass filter 38 (Model 3202™, Krohn-Hite Corporation, Brockton, Mass., USA). The filter output signal was digitized at 50 Mb/s using oscilloscope 28b (TDS744™, Tektronix, Inc., Beaverton, Oreg., USA) and saved to computer 28a. The filter was necessary to remove low frequency noise, presumably resulting from a combination of a structural resonance of the receiver and transient electrical signals from the high voltage discharge.

The remote broadband receiver (i.e., resonant acoustic scattering wave receiver 20a), was designed to measure resonant acoustic scatter without blocking the acoustic path between the lithotripter and the stone models. It was fabricated with a polyvinylidene fluoride (PVDF) film of 25 µm thickness and 50 mm diameter, formed with a spherical curvature having a radius of 150 mm. The custom receiver had a bandwidth of 50 kHz-10 MHz.

With the addition of a differential amplifier (not separately shown), the −3 dB pass band was between 100 kHz and 10 MHz. Focal properties of resonant acoustic scattering wave receiver 20a were characterized by wiring the PVDF film as a source, exciting it at 3.6 MHz, and measuring the resulting acoustic field with a hydrophone (GL-0150-1A, Specialty Engineering Acoustics, Soquel, Calif., USA). The axial and lateral dimensions of the pressure focus measured at −6 dB were 45 mm and 2 mm, respectively.

An effort was made to reduce cavitation in the initial experiments. Stone models were made of smooth, lens quality glass, because glass is smooth and bubbles do not adhere well to smooth wet glass. The lithotripter was operated at a low charging voltage of 17 kV to reduce the negative pressure of the shock wave. Successive shock waves were triggered at one minute intervals to enable bubbles to dissolve. Lastly, digital photography was used to create an image of the cavitation. A high-speed camera (Imacon 200™, DRS Technologies, Parsippany, N.J.), 105 mm lens, and 27.5 mm extender produced a 2.0 cm×2.4 cm field of view in 980 pixels×1200 pixels. Such images confirmed that the empirical data were collected substantially free of cavitational effects.

Calculated and measured signals were processed using MATLAB™ (The Mathworks, Inc., Natick, Mass., USA). Measured signals were de-convolved with a sampled approximation of the high pass filter's impulse response. De-convolution removed the transient effects of the filter, but also added high frequency noise, caused in part by division in frequency, which was removed with a 10 MHz low pass filter. Twenty measured waveforms were aligned in time to correct for jitter in the shock wave trigger timing, and then averaged. Averaging was intended to compensate for shot-to-shot variations in the shock pulse, but had little effect on the signals, since they were relatively repeatable. Time domain processing was not performed on signals obtained from calculation.

Specific results from these studies are described in greater detail below.

Figure 5:
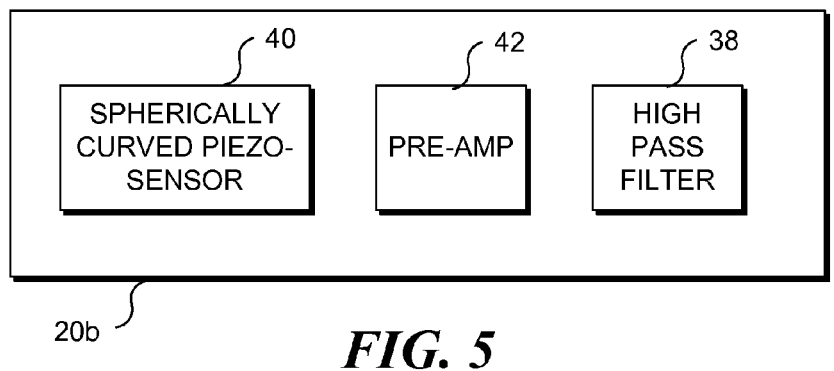
FIG. 5 is a functional block diagram illustrating one exemplary acoustic receiver for collecting a resonant acoustic scattering signal during shock wave therapy of a kidney stone.

FIG. 5 is a functional block diagram illustrating one exemplary acoustic receiver 20b, for collecting a resonant acoustic scattering signal during shock wave therapy of a kidney stone. As noted above, high pass filtering and amplification of the raw signal are desirable. Thus, filter 20b includes a pre-amp 42 and high pass filter 38, as well as a spherically curved piezoelectric sensor 40. While the acoustical receiver in the empirical system of FIG. 4 was based on a piezoelectric polymer, it should be recognized that a piezoceramic could alternatively be employed. It should be recognized that the curvature of the receiver is important, because a proper curvature maximizes the receiver's ability to collect the resonant acoustic scattering wave. In some embodiments, the filter and preamp can be implemented as separate components, rather than being integrated in the receiver.

Figure 6:
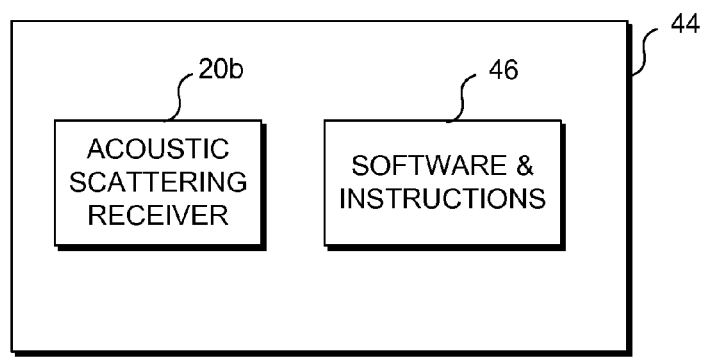
FIG. 6 is a functional block diagram illustrating one exemplary kit for enabling a prior art shock wave therapy system to collect and process a resonant acoustic scattering signal during shock wave therapy of a kidney stone, in accord with the concepts disclosed herein.

FIG. 6 is a functional block diagram illustrating one exemplary kit for enabling a prior art shock wave therapy system to collect and process a resonant acoustic scattering signal during shock wave therapy of a kidney stone, in accord with the concepts disclosed herein. Such a kit can be used to enable some pre-existing shock wave therapy systems to utilize the resonant acoustic scattering wave based techniques disclosed herein. A kit 44 includes resonant acoustic scattering receiver 20b, and software 46 (including written instructions for the software and use of the kit). Resonant acoustic scattering receiver 20b includes an output cable having a form factor configured to couple with an existing data port in the shock wave therapy system. For example, many such therapy systems include a port for coupling EKG sensors to the therapy system. Coupling receiver 20b to such an EKG port is merely one exemplary approach, as other systems may include other types of data ports. Receiver 20b is simply configured to couple to existing system data ports.

Software 46 includes an instruction set that when executed by a processor enables the processor to implement steps consistent with beneficially employing a resonant acoustic scattering signal collected by receiver 20b. As described in greater detail below, the resonant acoustic scattering signal can be used in a variety of ways, including but not limited to: (1) providing a clinician with an indication that the kidney stone being treated has been fragmented; (2) providing a clinician with an indication that the kidney stone cannot be substantially comminuted with the remaining allowable dose (such that therapy should be discontinued); (3) automatically preventing the administration of additional shock waves upon determining that the kidney stone cannot be substantially comminuted with the remaining allowable dose; (4) providing a clinician with an indication that the kidney stone has been substantially comminuted (such that therapy should be discontinued); (5) automatically preventing the administration of additional shock waves upon determining that the kidney stone has been substantially comminuted; and, (6) automatically administering a pre-determined number of additional shock waves and then preventing the administration of additional shock waves upon determining that the kidney stone has been substantially comminuted. These functions are not intended to be limiting on this novel approach.

It should be recognized that the processing resources available in existing shock wave therapy systems vary from system to system. In systems that include fluoroscopic imaging components or ultrasound imaging components, the imaging components generally incorporate processors that can be configured (via the use of software included in the kit) to perform the above-noted processing of the resonant acoustic scattering signal. In shock wave therapy systems that do not include an imaging component (or more significantly, do not include a processor/controller that can be programmed to implement the processing of a resonant acoustic scattering signal), it may be necessary to incorporate a processor into the kit. Such a processor can be an ASIC, a custom logic circuit, or a software-based processor. While including a processor in the kit will increase the cost of the kit, because of the relatively small processing resources required, and the relatively modest cost of minimally functional processors, incorporating a processor into the kit may still be economically feasible. For example, computers are routinely upgraded by the addition of application-specific processing cards. Such application-specific processing cards can be very inexpensive. Thus, the incorporation of a processing component into such a kit is not unreasonable.

It should also be recognized that other kits can be configured to implement additional aspects of the concepts disclosed herein. For example, to monitor displacement of kidney stones/kidney stone fragments during therapy (generally as described above), resonant acoustic scattering receiver 20b could be replaced with a Doppler ultrasound imaging transducer (to generate a pressure pulse of known amplitude and to acquire displacement data), and software 46 can include an instruction set that when executed by a processor enables the processor to implement steps generally consistent with the two exemplary displacement based techniques described in detail below. It should be recognized that other acoustic sources and receivers could be employed in place of a Doppler ultrasound unit.

Figure 7:
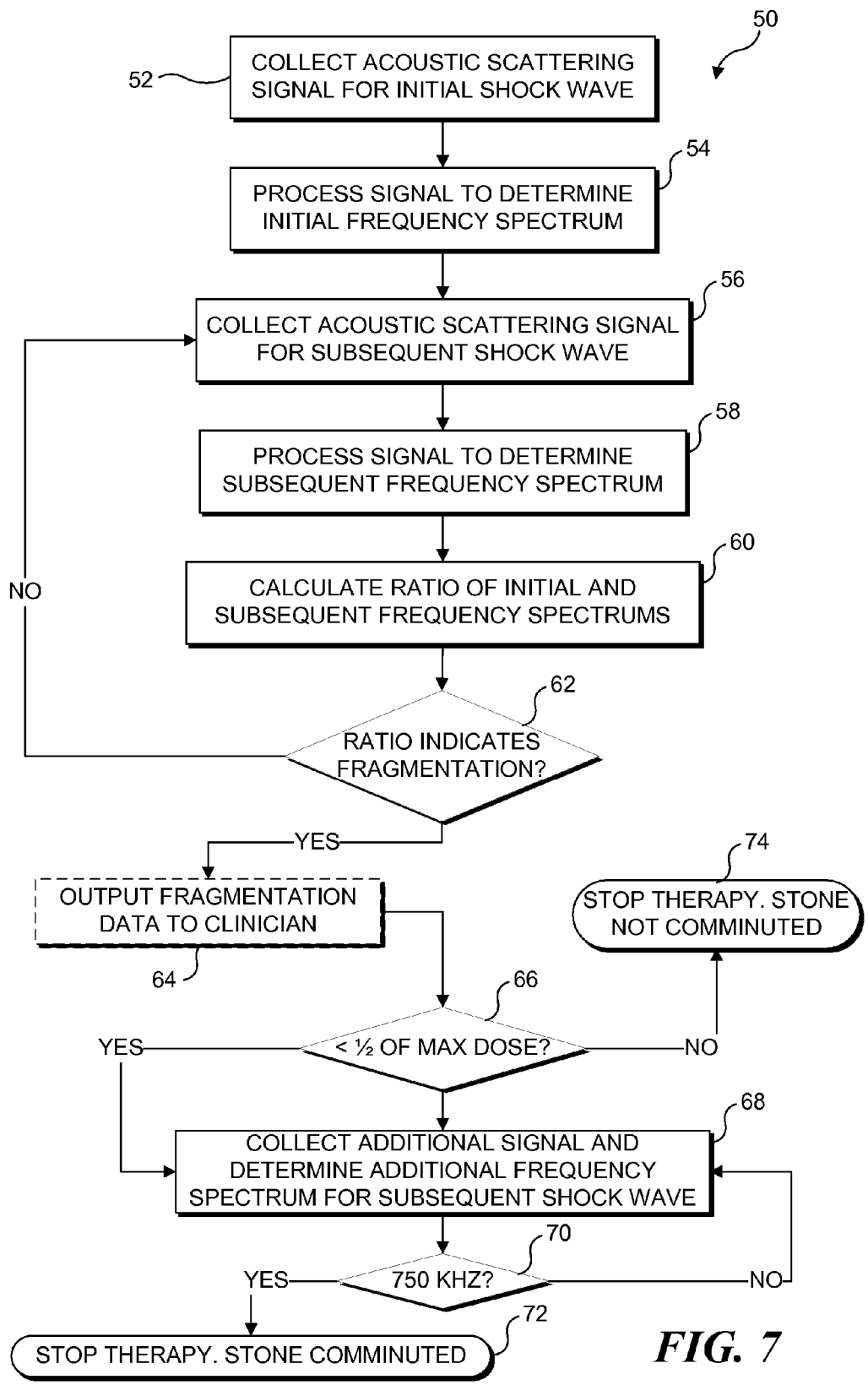
FIG. 7 is a flow chart of exemplary steps for acquiring and utilizing a resonant acoustic scattering signal during shock wave therapy of a kidney stone.

FIG. 7 is a flow chart 50 of exemplary steps for acquiring and utilizing a resonant acoustic scattering signal during shock wave therapy of a kidney stone. It should be recognized that many modifications to such steps are encompassed within the scope of the disclosure provided herein. As such, these steps are simply exemplary, and not limiting.

In a block 52 a resonant acoustic scattering signal is collected (generally as described above; specifically, a resonant acoustic scattering wave is detected by a receiver that produces a signal indicative of the resonant acoustic scattering wave) for an initial shock wave impacting on a kidney stone. In a block 54, the collected signal is processed to determine an initial frequency spectrum. In a block 56, a resonant acoustic scattering signal is collected for a subsequent shock wave. In a block 58, the resonant acoustic signal subsequently collected is processed to determine a subsequent frequency spectrum. Then, in a block 60, a ratio between the initial and subsequent frequency spectrums is calculated.

In a decision block 62, a determination is made as to whether the ratio indicates that the kidney stone has been fragmented (regardless of the relative sizes of the fragments, i.e., regardless of whether the kidney stone has been substantially comminuted). If the ratio indicates that the kidney stone has not yet been fragmented, an acoustic scattering signal is again collected for a subsequent shock wave (see block 56). However, if the ratio indicates that the kidney stone has been fragmented, the fragmentation data last collected can be output to a clinician in an optional block 64. A determination is then made as to whether it has taken less than one half of the maximum allowed dosage to fragment the kidney stone (as indicated in a decision block 66). If so, an acoustic scattering signal is collected for the subsequent shock wave, and an additional frequency spectrum is determined, as indicated in a block 68. If however, more than half of the maximum dose was used to fragment the kidney stone, then the shock wave therapy is terminated (as indicated in a block 74) without substantially comminuting the kidney stone. The logic behind halting therapy at this point is that if more than one half of the maximum allowed dosage has not been able to fragment the kidney stone, then it is likely that the remaining one half of the maximum allowed does will be insufficient to substantially comminute the kidney stone (i.e., will not achieve the desired outcome), and the inherent risks of administering the maximum allowed dosage without achieving the desired outcome suggests that additional therapy is not in the patient's best interest. For example, detecting fragmentation during the first 500 to 1000 shock waves could help a clinician decide to cease or continue shock wave therapy. In the case that the stone has not yet fragmented, a clinician can halt the procedure to reduce shock wave exposure and minimize dose-dependent side effects. Otherwise, the procedure can be allowed to continue, and the clinician would know that the desired effect will likely be achieved.

Assessing fragmentation early in the shock wave therapy (early being within the first 1000 of a possible 4000 shock waves) is currently difficult to achieve with imaging methods commonly used in shock wave therapy. Large particles may not have moved enough to be distinguished, and cracks may be hidden from view, depending on the stone's orientation relative to the imaging sensor. If the stone is not positioned to reveal a fracture, even an imaging modality with sub-millimeter resolution may not detect fragmentation.

Returning once again to block 68, once the resonant acoustic scattering signal has been collected for a subsequent shock wave, and a subsequent frequency spectrum has been determined, then in a decision block 70, a determination is made as to whether that frequency spectrum is indicative of a fully comminuted kidney stone. Empirical studies conducted to develop this technology have indicated that kidney stone fragments of about 2 mm in size have a characteristic resonant acoustic scattering frequency of about 750 kHz. Particles of that size can be naturally passed through the urinary tract. Thus, particles of that size represent a substantially comminuted kidney stone. If it is determined in decision block 70 that the kidney stone is not substantially comminuted (i.e., the resonant acoustic scattering frequency is lower than 750 kHz), then an additional resonant acoustic scattering signal and corresponding frequency spectrum are determined for a subsequent shock wave (the logic returns to block 68). If however it is determined in decision block 70 that the kidney stone is substantially comminuted (i.e., the resonant acoustic scattering frequency is substantially greater than or equal to about 750 kHz), then the therapy is terminated in a block 72. It should be recognized that 750 kHz represents a useful endpoint; however, other frequencies can be selected. Furthermore, as higher frequencies are associated with smaller fragments, some clinicians may prefer to continue treatment until a higher resonant acoustic scattering frequency is achieved, to ensure full comminution. Thus, the use of 750 kHz as an indicator of the endpoint of shock wave therapy of kidney stones is intended to be exemplary, rather than limiting.

As noted above, 750 kHz represents a reasonable approximation. A more precise value for the resonant acoustic scattering frequency can be determined if the speed of sound in a particular kidney stone is known. The actual frequency is a function of the speed of sound c in a particular kidney stone, such that frequency=(c/2)(stone size). It is generally accepted that 2 mm corresponds to a stone size that will readily pass through a patients urinary tract, such that if c is known the frequency corresponding to a 2 mm stone size can be calculated (of course, frequencies corresponding to other sizes can be determined; thus, if a clinician wanted the fragments to be 1 mm, the corresponding frequency to use as an endpoint could be determined if the speed of sound in that kidney stone is known or can be reasonably estimated). The 750 kHz value was determined using c for an average kidney stone of a certain type. In some treatments, the stone type is known for a patient, thus c can be readily inferred. Empirical data have been used to classify kidney stones into different types, in which the speed of sound varies from about 2000 m/s to about 4000 m/s. When the kidney stone type is known, there are lookup tables available to correlate sound speed with the known type. The 750 kHz value is based on a speed of sound of 3000 m/s and a desired fragment size of 2 mm.

It should also be recognized that c can be empirically determined; for example, by using X-rays to size the original kidney stone, and using the initial resonant acoustic scattering frequency data collected after applying an initial shock wave to determine c based on the measured stone size and measured frequency. Furthermore, using a variety of different simulated kidney stones, the 750 kHz value correlates with kidney stone fragments ranging from about 1 mm to about 3 mm, a size range that is effectively passable (i.e., substantially comminuted).

As noted above, many variations of this method can be implemented. The method of FIG. 7 can be considered to have two primary functions, each of which can be implemented as a separate method. Those functions are determining when the kidney stone is initially fragmented (for example, see decision block 62), and determining when the kidney stone is substantially comminuted (for example, see decision block 70). It should be recognized that those techniques can be implemented independently (although, in at least one exemplary embodiment, the techniques are implemented together).

With respect to block 72, where the therapy is terminated after the frequency spectrum indicates that the kidney stone is substantially comminuted, it should be recognized that some clinicians may determine that it would be beneficial to administer one or more additional shock waves to ensure that the kidney stone is fully comminuted. For example, a clinician may determine that it would be desirable to administer a hundred additional shock waves (a normal dose ranging from about 2000 to 3000 shock waves, with 4000 shock waves generally corresponding to a maximum allowable dose).

With respect to optional block 64, it should be recognized that no specific output to the clinician is required (i.e., the shock wave therapy system can be automatically controlled, such that therapy is terminated in block 74 without previously informing the clinician of the status of the stone fragmentation). It is likely that clinicians will desire an indication of fragmentation. That indication can be provided continuously, intermittently, or after specific milestones are reached (i.e., one indication after an initial fragmentation, and another indication after substantial comminution has been achieved). Thus, the specific location of block 64 relative to the other method steps is intended to be exemplary, rather than limiting.

Figure 8:
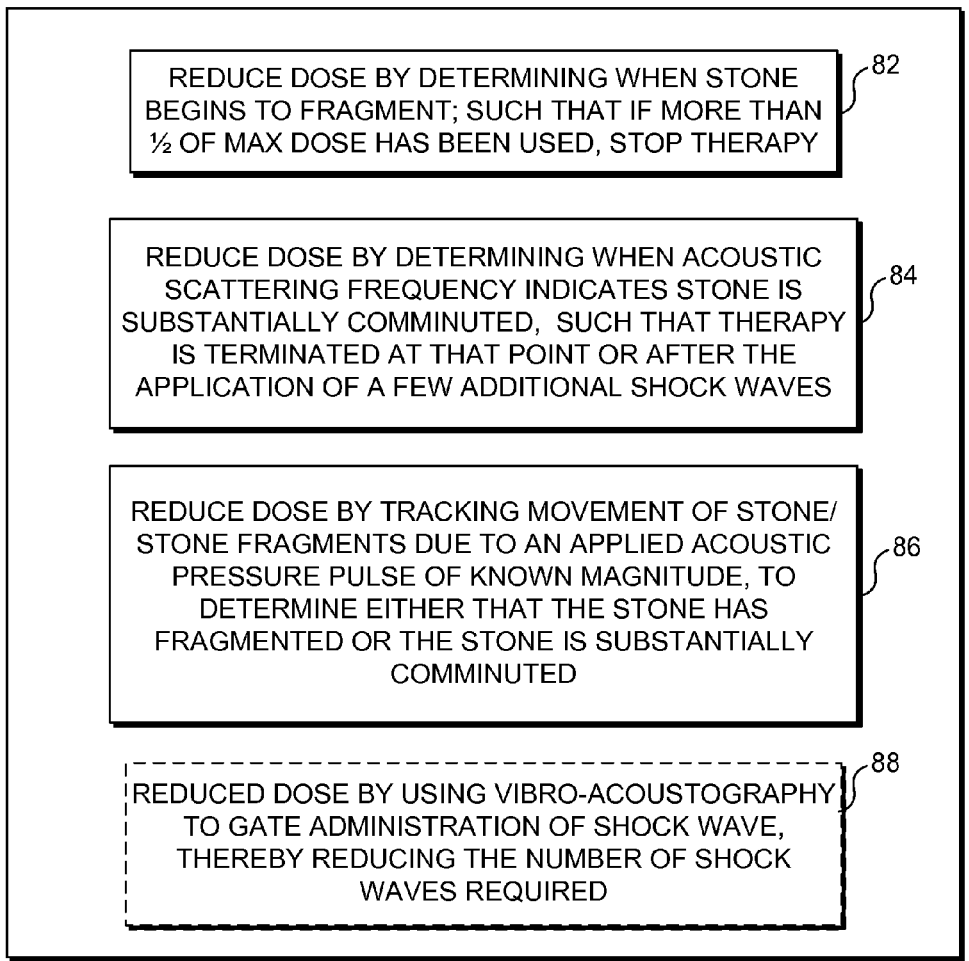
FIG. 8 is a functional block diagram of exemplary techniques for reducing the dose administered to a patient during shock wave therapy.

FIG. 8 is a functional block diagram 80 showing four exemplary techniques disclosed herein for reducing the dose administered to a patient during shock wave therapy. Some, but not all, of these techniques are based on using the resonant acoustic scattering signal described above. It should be recognized that these techniques can be implemented individually, or in any desired combination.

In a block 82, the dose administered to a patient during shock wave therapy is reduced by determining when the kidney stone being treated begins to fragment, such that if more than one half of the maximum allowed dosage is utilized to reach that point, therapy will normally be halted. As discussed above, the logic behind this technique is a recognition that if more than half of the maximum allowed dose is required to initially fragment the kidney stone, then the remaining available dosage may be insufficient to substantially comminute the kidney stone. Halting the treatment (which will not likely reach its desirable outcome) will reduce the chance that a patient will suffer negative consequences as a result of receiving the maximum allowed dosage, but without the desired result being achieved. This approach can be considered as reducing the dose administered to a patient, because previous techniques have often simply applied the maximum allowable dose (most clinicians are not able to confidently ascertain that a kidney stone is substantially comminuted, using available imaging technologies). This technique enables the clinician to halt treatment early when an indication is obtained that the treatment will not reach the desired outcome. This process is substantially equivalent to that described above with respect to decision block 62 of FIG. 7.

In a block 84 the dose administered to a patient during shock wave therapy is reduced by determining when the resonant acoustic scattering frequency spectrum indicates that the stone is substantially comminuted. As discussed above, empirical evidence has indicated that a resonant acoustic scattering frequency of about 750 kHz corresponds to kidney stone fragments of about 2 mm in size. Thus, such a frequency can be considered to be an endpoint indicator for terminating shock wave therapy of kidney stones (noting that other frequencies can be used as an endpoint indicator based on the frequency being a function of the speed of sound in the stone and the desired fragment size). Certain clinicians may wish to administer a limited number of additional shock waves to ensure that the kidney stone is fully comminuted. This technique can be considered as reducing the dose administered to a patient, because previous techniques have often simply applied the maximum allowable dose (most clinicians are not able to confidently ascertain that a kidney stone is substantially comminuted using available imaging technologies). Rather than simply administering the maximum allowed dose, this technique provides an unambiguous endpoint indication for early termination of the shock wave therapy. This technique is substantially equivalent to that described above with respect to decision block 70 of FIG. 7.

In a block 86, the dose administered to a patient during shock wave therapy is reduced by determining when a displacement of kidney stone fragments induced by an applied acoustic pressure pulse of known magnitude indicates that the kidney stone is either fragmented or substantially comminuted. Thus, displacement measurements can be useful in two different ways, which are described in greater detail with respect to FIGS. 14A and 14B. It should be recognized that these two different techniques can be used independently, or together, or with one or more of the additional techniques disclosed herein. Essentially, these techniques makes use of the phenomenon that a pressure wave will result in a relatively larger displacement when applied to relatively smaller particles, and a relatively smaller displacement when applied to relatively larger particles.

In a first exemplary embodiment involving utilizing displacement measurements, the displacement of an intact kidney stone due to an applied pressure pulse of known magnitude is measured. As shock wave therapy proceeds, additional displacement measurements are made, using the same magnitude pressure pulse. While the stone is intact, the displacement measurements should be substantially unchanged. When the stone is fragmented, the relatively smaller fragments will experience a relatively larger displacement, such that the displacement measurement is indicative of fragmentation. This result is significant, because fluoroscopic and ultrasound images make it difficult to differentiate a mass of closely spaced kidney stone fragments from an intact kidney stone. The displacement measurements for a mass of closely spaced kidney stone fragments will be very distinguishable from the displacement measurement for an intact kidney stone. The displacement data are thus indicative of fragmentation, and once fragmentation is indicated, a clinician can terminate therapy, or apply a relatively small number of additional shock waves to ensure that the mass of fragments becomes substantially comminuted. Note that once the transition between an intact kidney stone and kidney stone fragments occurs, additional shock waves will either provide further fragmentation (which will result in additional increases in the displacement measurements), or little additional fragmentation will occur (in which case no additional increase in the displacement measurements will be noted). Thus, the displacement measurements will not only indicate when fragmentation has occurred, but also can be used to indicate whether additional shock waves will result in further fragmentation. Acquisition of the displacement data will likely require employing a slower pulse repetition frequency for the shock waves, which will likely result in an increase in overall treatment times. However, the increase in treatment times will likely be offset by the reduced dose required to achieve a desirable therapeutic outcome (i.e., substantial fragmentation of the kidney stone, sufficient to enable the fragments to pass through the urinary tract naturally). This technique can be considered as reducing the dose administered to a patient, because previous techniques have often simply applied the maximum allowable dose (most clinicians are not able to confidently ascertain that a kidney stone is substantially comminuted using available imaging technologies). It should be recognized that once the displacement data are used to determine that the stone has been fragmented, a determination of whether one half of the maximum allowed dosage has been administered to a patient can be made to decide whether therapy should be terminated or continued, generally as described above with respect to determining fragmentation using a ratio of resonant acoustic scattering frequencies (i.e., block 66 of FIG. 7).

In a second exemplary embodiment utilizing displacement measurements, empirical data collected during the fragmentation of kidney stones (and synthetic kidney stones) enable a correlation to be determined between the displacement of kidney stone particles (under an applied pressure pulse of the known magnitude) and particles of the specific size. Once such a correlation has been identified, observation of displacement data collected during shock wave therapy of the kidney stone can enable the displacement data to be used as an endpoint determination for terminating therapy. It should be noted that the fragments may need to be relatively dispersed to enable accurate sizing of individual fragments to be achieved. Repeated displacement measurements during therapy (i.e., cyclically applying a shock wave and then applying a pressure pulse of known magnitude and measuring displacement) will likely encourage dispersal of the kidney stone fragments (the cyclically applied pressure pulse utilized to measure displacement will encourage dispersion), making a size determination for individual fragments easier to achieve. It should be recognized that such dispersion, which also will occur where displacement measurements are used to indicate an endpoint for early termination of therapy as described immediately above, should make ultrasound and fluoroscopic images of fragmented kidney stones easier to interpret (i.e., the dispersed fragments will be more easily visualized by such technologies than will be a mass of closely spaced kidney stone fragments). This technique can be considered as reducing the dose administered to a patient, because previous techniques have often simply applied the maximum allowable dose (most clinicians are not able to confidently ascertain that a kidney stone is substantially comminuted using available imaging technologies). Rather than simply administering the maximum allowed dose, this technique provides an unambiguous early endpoint indication for terminating the shock wave therapy.

These techniques are described in greater detail in connection with the description of FIGS. 13, 14A, and 14B. Note that the relative weight and tissue mass of an individual patient may affect the correlation between displacement data collected for a specific patient and the empirical data used for correlation. This effect can be compensated by measuring the attenuation of the amplitude of the shock wave or ultrasound reflected from the stone. By knowing this attenuation, the effect attenuation has on the displacement correlation can be compensated in any patient.

Further, it should be noted that the dispersion of the fragments can be combined with conventional ultrasound or fluoroscopic imaging to provide an indication of fragmentation, even if no displacement measurements are obtained. Note that in an ultrasound image or a fluoroscopic image, tightly packed fragments are difficult to distinguish from intact stones. When the applied pressure wave and imaging are performed together, the dispersal caused by the applied pressure wave or pulse will enable fragments to be readily distinguished from intact stones (because the pulse will push the fragments apart, making them easier to distinguish from an intact stone in the image).

With respect to displacement related techniques, it should further be noted that the pressure pulses delivered to enable displacement measurements to be acquired (or to facilitate differentiation of fragments from intact stones in ultrasound or fluoroscopic images) may have yet another beneficial effect. As noted above, such pressure pulses will generally facilitate dispersion of the kidney stone fragments. In addition to making it easier to estimate the size of any specific particle based on its displacement, such dispersion may also facilitate removal of the particles from the kidney. In and of itself, facilitating the removal of fragmented kidney stone particles from the kidney is an important aspect of the concepts disclosed herein. It should also be noted that where X-ray imaging data of a kidney stone are available, the X-ray imaging data will provide information about the density of the stone, which can be used to improve the estimate of stone size based on displacement.

In a block 88, the dose administered to a patient during shock wave therapy is reduced by determining when the kidney stone is properly positioned relative to the focal point of the shock wave, such that the shock wave is triggered only when the kidney stone is positioned to be impacted by the shock wave. This concept is described in greater detail below. Essentially, this concept employs vibro-acoustography to gate administration of the shock wave, which can be considered as reducing the dose administered to a patient, because empirical evidence indicates that improper targeting of conventional shock wave therapy means that many shock waves miss the kidney stone. Empirical data collected in developing this concept show that fewer shock waves are required to fully comminute synthetic kidney stones when this vibro-acoustography gating technique is employed, compared to a number of shock waves required to fully comminute synthetic kidney stones without using the gating technique. Fewer shock waves means a lower dose is administered to achieve the same desired comminution. This technique is described in greater detail in connection with the description of FIGS. 15, 16, 17A, and 17B. It should be recognized that block 88 is shown in dashed lines, indicating that block 88 is preferably not implemented individually, but only in combination with one or more of the other dose reduction techniques described in connection with FIG. 8.

Figure 9:
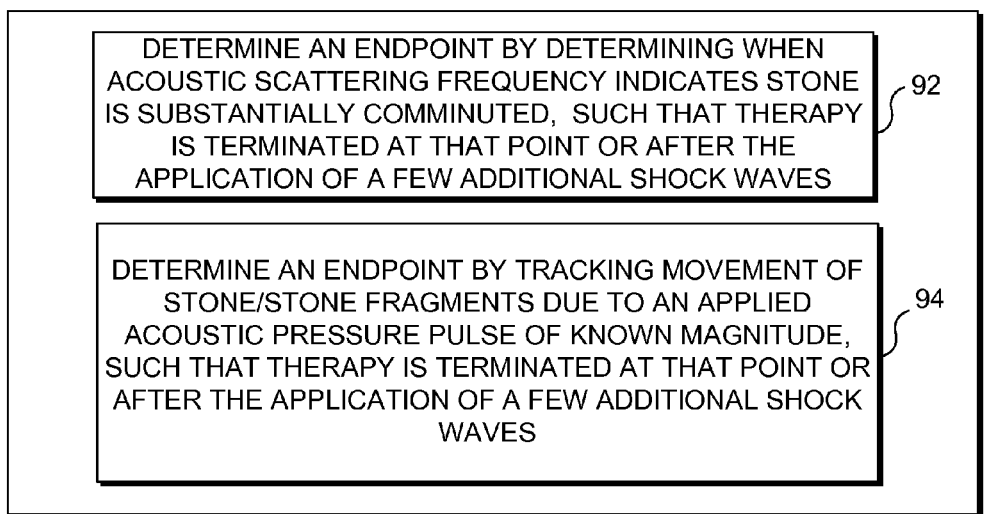
FIG. 9 is a functional block diagram of exemplary techniques for determining an endpoint at which to terminate shock wave therapy of a kidney stone.

FIG. 9 is a functional block diagram 90 illustrating two exemplary techniques that are disclosed herein for determining an endpoint for terminating shock wave therapy of a kidney stone. One of these techniques is based on using the resonant acoustic scattering signal described above. It should be recognized that these techniques can be implemented individually, or in combination.

In a block 92, an endpoint for terminating shock wave therapy of the kidney stone is determined when the frequency of the resonant acoustic scattering signal indicates that the kidney stone is fully comminuted. This endpoint has been generally described above with respect to block 70 in FIG. 7 and block 84 of FIG. 8.

In a block 94, an endpoint for terminating a shock wave therapy of the kidney stone is determined when displacement data of kidney stone fragments collected in response to the application of an acoustic pressure pulse correlate with empirical displacement data for fully comminuted kidney stones exposed to an equivalent acoustic pressure pulse, or when subsequent displacement measurements indicate no additional size reduction occurs after additional shock waves are administered. These two different displacement based endpoints have been generally described above with respect to block 86 of FIG. 8. Additional description can be found in connection with the discussion of FIGS. 14A and 14B.

FIG. 10 graphically illustrates a de-convolution of a resonant acoustic scattering signal acquired by the empirical system of FIG. 4 and a simulated kidney stone, the de-convolution correcting an artifact induced by the high pass filter. As noted above, a high pass filter is used to remove low-frequency signals created by other resonant modes of the receiver, but the high pass filter distorts the signal. Distortion from the impulse response of the filter is removed by de-convolution. The filter's impulse response was found by measuring and recording its step response, and then using a difference equation to approximate the derivative. After re-sampling the impulse response to match the sampling rate of the measurements, data were de-convolved by division in frequency. Numerical errors were reduced by adding a small number to the quotient for transforming back to the time domain. An example signal before and after de-convolution is shown in FIG. 10, with a line 100 corresponding to the signal before de-convolution, and a line 102 corresponding to the signal after de-convolution.

FIGS. 11A-11D and 12A-12D represent various signal processing steps implemented after de-convolution. Significantly, FIGS. 11A-11D involve synthetic data (i.e., data calculated from a scattering model) while FIGS. 12A-12D involve empirical data acquired using the system of FIG. 4 and the two stone models discussed above with respect to FIG. 4 (i.e., the solid glass sphere and the two glass hemispheres joined by an adhesive).

After de-convolution, measured signals were normalized and each signal was divided by its root mean square value. Normalization was done to compare scatter from the two stone models based on frequency, but not amplitude. Next, signals were aligned in time and averaged. From this point, the synthetic signals (obtained from calculations), which were also normalized, and the signals from actual measurements were processed identically.

FIG. 11A graphically illustrates a pressure versus time curve 104 based on a resonant acoustic scattering signal of an intact simulated kidney stone, whereas FIG. 11B graphically illustrates a pressure versus time curve 106 based on a resonant acoustic scattering signal of a fractured simulated kidney stone, the resonant acoustic scattering signal for each Figure having been theoretically calculated. The synthetic resonant acoustic scattering signal was calculated by averaging radiation from a model stone (both intact and fragmented) over the surface of the acoustic receiver.

FIG. 12A graphically illustrates a voltage versus time curve 114 based on a resonant acoustic scattering signal of an intact simulated kidney stone, whereas FIG. 12B graphically illustrates a voltage versus time curve 116 based on a resonant acoustic scattering signal of a fractured simulated kidney stone, the resonant acoustic scattering signal for each Figure having been acquired by the empirical system of FIG. 4. With respect to the signals of FIGS. 12A and 12B, it should be noted that good reproducibility was obtained from subsequent testing, and that the empirically obtained signals generally agree well with the synthetic signals of FIGS. 11A and 11B.

Frequency analysis for the synthetic and empirical signals was performed in four steps. First, a segment of each signal identified as the shock wave reflection (i.e., the first 5 μs for each of the signals in FIGS. 11A, 11B, 12A, and 12B) was truncated (the fact that this portion of the signal was similar for both stone models, fragmented and intact, indicates that the first 5 μs of the signal corresponds to the shock wave reflection, as opposed to the resonant acoustic scattering signal being sought). The 15 μs segment following the signal wave reflection was retained for each signal (recognizing that this portion of the signal most likely corresponded to the resonant acoustic scattering signal being sought). Note that t=0 is considered to be the time that the shock wave impacts the kidney stone.

FIGS. 11A, 11B, 12A, and 12B are in the time domain, with FIGS. 11A and 11B (corresponding to synthetic data) being expressed in terms of pressure, and FIGS. 12A and 12B (empirical data collected using the system of FIG. 4) being expressed in the terms of voltage. The synthetic data illustrate sinusoidal waveforms with periods of approximately 2.3 μs and 1.2 μs for the intact and fractured stones, respectively. The empirical data illustrate sinusoidal waveforms with periods of approximately 2.6 μs and 0.9 μs for the intact and fractured stones, respectively. These periods correspond to the time it would take sound to travel twice across the largest diameter of the stone model, once to a distal side and then back to a proximal side. The effects of the 1 mm epoxy layer (used to simulate a fracture in the simulated fractured stone, generally as described above) are readily identifiable in both the synthetic data and in the empirical data corresponding to the fractured stone model. Resonant acoustics scatter from the fractured stone model has noticeably higher frequency, since the reverberation times are shorter, and a slightly higher amplitude, because the flat sides of the glass hemispheres were perpendicular to the shock wave axis.

Referring once again to the four steps involved in the frequency analysis performed on the resonant acoustic scattering signal, in a second step, the power spectral density of each signal was determined. FIG. 11C graphically illustrates the power spectral densities for the synthetic signals for the fractured and intact kidney stone, while FIG. 12C graphically illustrates the power spectral densities for the empirical signals for the fractured and intact kidney stone. Thus, FIG. 11C graphically illustrates a power frequency curve 110 for the intact stone and a power frequency curve 112 for the fractured stone. Similarly, FIG. 12C graphically illustrates a power frequency curve 118 for the intact stone and a power frequency curve 120 for the fractured stone.

Having obtained the power spectral densities for each signal, the third step was employing integration to find energy in specific frequency bands. The following relationship was employed:

$$E = \int_{f_1}^{f_2} W \, df, \quad (1a)$$

where E is energy, $f_1$ and $f_2$ are the frequency end points of each band, and W is the power spectral density. An alternate form of this relationship is:

$$E = \sum_{k=f_1/\Delta f}^{f_2/\Delta f} W_k \cdot \Delta f \quad (1b)$$

where $W_k$ is the discrete power spectral density sequence at frequency $f = k \Delta f$, k is an index variable, $f_1$ and $f_2$ are endpoints of the aforementioned frequency bands, and $\Delta f$ is the difference between adjacent samples in frequency.

The fourth step was generating the ratio noted above with respect to FIG. 7 (block 62). In that ratio, the energies for fractured stones, $E_F$, were divided by energies for intact stones, $E_I$. Thus, $$R = \frac{E_F}{E_I} \quad (2)$$

where $E_F$ and $E_I$ are calculated using Eq. (1a).

The ratio of energies, R, is intended to display the redistribution of energy and frequency after the stone model was fractured into two pieces. FIG. 11D graphically illustrates the frequency ratio (i.e., R) based on the synthetic resonant acoustic scattering signals, whereas FIG. 12D graphically illustrates the frequency ratio based on the empirical resonant acoustic scattering signals acquired by the empirical system of FIG. 4. In each case, a sharp increase in the ratio magnitude occurs after 0.5 MHz, providing an indication that the simulated kidney stone initially begins to fragment for frequencies above about 500 kHz. It should be noted that the ratio generated from the synthetic data suggests that fragmentation is indicated when R is approximately 2. The frequency ratio based on the empirical data suggests that fragmentation is indicated when R is greater than 3. For both the synthetic data and the empirical data, for frequencies below 500 kHz, the frequency ratio is significantly less than 2. In other words, both the synthetic data and the empirical data show increased energy in the frequency band between about 0.5 and 2.0 MHz, clearly indicating that the fractured stone model can be distinguished from the intact stone model based on such a ratio. This data set provided a basis for formulating the technique described above, where resonant acoustic scattering signals are acquired and processed to determine when a kidney stone has fragmented during shock wave therapy, by collecting an initial resonant acoustic scattering frequency spectrum and a subsequent resonant acoustic scattering spectrum, determining a frequency ratio, and concluding that the kidney stone had been fragmented after the ratio was greater than about 2 (see blocks 60 and 64 from FIG. 7). Furthermore, this data set also provided a basis for formulating the technique described above, where resonant acoustic scattering signals are acquired and processed to determine when a kidney stone is substantially comminuted, where it is concluded that a kidney stone is substantially comminuted once the resonant acoustic scattering frequency has reached about 750 kHz (or some other frequency based on the desired fragment size and the speed of sound in the kidney stone being fragmented). Note that the empirical data seemed to indicate that fragmentation begins after about 500 kHz. However, the data from FIGS. 11D and 12D (i.e., all the synthetic data and the empirical data) were integrated in two different segments. A first segment ranged from 0 kHz to 500 kHz, and a second segment ranged from 500 kHz to 2000 kHz. So while such data clearly indicates that fragmentation has occurred after 500 kHz, the data from FIGS. 11D and 12D do not indicate at what point above 500 kHz that fragmentation has been initiated, and at what point it can be concluded that is kidney stone has been substantially comminuted. Note that because the data segment ranging from 500 kHz to 2000 kHz has been integrated, no change in the ratio occurs even though one might surmise that particle size is decreasing as frequency increases. Indeed, later studies have confirmed that for non-integrated frequency segments, the ratio increases as frequency increases, because particle size is decreasing. Significantly, the synthetic data indicated that the resonant acoustic scatter frequency for an intact stone should be about 280 kHz, and about 560 kHz for a fractured stone. The empirical data correlates well with this indication, since the fractured stone clearly has a resonant acoustic scatter frequency greater than 500 kHz.

It should be noted that the initial shock wave and resonant acoustic scattering studies were conducted while using high-speed photography to monitor the ambient environment of the simulated kidney stones, to determine what role cavitation might have in generating the resonant acoustic scattering signal. These high-speed photographs indicate that very small bubbles were generated only after about 26 μs, and that collapse of such bubbles generally occurred between about 250 μs and about 350 μs. The resonant acoustic scattering signal discussed above represents data collected between about 5 μs and about 20 µs, after the shock wave reflection (before 5 µs), and before any acoustical signal corresponding to cavitation could be collected (after about 250 µs). Therefore, it should be recognized that the data collected by an acoustic receiver configured to receive a resonant acoustic scattering wave propagating outwardly and away from a kidney stone after the impact of a shock wave will include an initial portion corresponding to shock wave reflection (before 5 µs), a subsequent portion corresponding to resonant acoustic scattering (from about 5 µs to about 20 µs), and a latter portion that can include cavitational components. Thus, one aspect of the concepts disclosed herein is properly segmenting the signal received and selecting only the portions of the signal corresponding to the resonant acoustic scattering wave.

As discussed above, an additional concept disclosed herein relates to determining an endpoint for terminating shock wave therapy of a kidney stone by measuring the displacement of kidney stone fragments, with an understanding that relatively smaller fragments will be displaced a relatively greater amount under the influence of an applied acoustic pressure pulse. FIG. 13 schematically illustrates an empirical system employed to correlate a displacement of simulated kidney stone fragments induced by a pressure pulse of a known magnitude to a particular particle size, to develop a displacement based endpoint for terminating shock wave therapy. Such a system includes shock wave source 16, ultrasound imaging probe 122 (for providing an acoustic pressure pulse 126 of known magnitude and measuring particle displacement; it is noted that other types of acoustic pressure sources and components for monitoring displacement could be employed, the ultrasound imaging probe simply representing an exemplary implementation, with a Doppler ultrasound probe representing one exemplary embodiment), and a sample container 124 holding a simulated kidney stone 128. It should be recognized that such a system is configured to obtain empirical data indicating how large a displacement kidney stone fragments of about 2 mm (i.e., a size corresponding to a fully comminuted kidney stone) experience when exposed to acoustic pressure pulses of various magnitudes. To actually implement a technique for determining an endpoint for terminating shock wave therapy of a kidney stone by tracking displacement data, the shock wave therapy system will require a source for applying a pressure pulse of a specific magnitude, and means for determining displacement of the stone particles. Doppler ultrasound devices can be beneficially employed to perform all of these functions. Either a separate controller, or the therapy system's own controller, would then need to be configured to analyze the collected displacement data and determine whether the displacement data corresponds to a particle size representing a fully comminuted kidney stone.

FIG. 14A is a flow chart 121 of exemplary steps for using displacement measurements obtained during shock wave therapy of a kidney stone to determine whether a kidney stone has been fragmented. In a block 123, the displacement of an intact kidney stone due to an applied pressure pulse of known magnitude will be measured. As shock wave therapy proceeds, additional displacement measurements will be made, using the same magnitude pressure pulse, as indicated in a block 125. In a decision block 127, a determination is made as to whether an increase in the displacement measurements has been noticed. While the stone is intact, the displacement measurements should be substantially unchanged. When the stone is fragmented, the relatively smaller fragments will experience a relatively larger displacement, such that the displacement measurement increases, the increase being indicative of fragmentation. If no such increase is detected, one or more additional shock waves are administered, and a subsequent displacement measurement is performed, as indicated in block 125. If in decision block 127, it is determined that displacement has increased, such an increase can be considered to be an endpoint for terminating the therapy, and therapy can be halted immediately, or a relatively small number of additional shock waves can be administered to ensure that the kidney stone is substantially comminuted. Alternately, the detection of an increase in decision block 127 could simply be an indication that the stone has fragmented (although the fragments may not yet be small enough for the stone to be considered to be substantially comminuted). FIG. 14A also illustrates optional additional steps, to be implemented, where decision block 127 is considered to be an indication of fragmentation, and not an endpoint. Referring to decision block 127, if it is determined that the measured displacement has increased, indicating that the intact kidney stone has fragmented, additional shock waves are administered, and a subsequent displacement measurement is performed, as indicated in a block 131. In an optional decision block 133, a determination is made as to whether the displacement has increased again. If the additional shock wave has resulted in additional fragmentation, the displacement measurement should increase again, indicating that the additional shock wave administered resulted in additional fragmentation. Thus, in decision block 133, if an increase in displacement is determined, even more shock waves can be administered, with yet another subsequent displacement measurement being made. At some point, additional shock waves are unlikely to further fragment the kidney stone particles, and no additional increase in displacement will be indicated in decision block 133. At that point, therapy can be halted, as indicated in block 129. It should be noted that instead of halting therapy after fragmentation has been identified, a determination can be made of whether one half of the maximum allowed dosage has been administered to a patient, to determine whether therapy should be terminated or continued, generally as described above with respect to determining fragmentation using a ratio of resonant acoustic scattering frequencies (i.e., block 66 of FIG. 7).

It should be recognized that many modifications can be made to such a technique. For example, the number of shock waves administered before taking a displacement measurement can be varied. Thus, as many as one hundred shock waves might be applied before taking the initial displacement measurement, particularly where experience has indicated that a particular type of kidney stone will not be fragmented until at least one hundred shock waves have been applied. The pulse repetition frequency for shock waves administered before taking a displacement measurement can be varied as therapy progresses. For example, early in the therapy session, it may be less beneficial to take frequent displacement measurements. As therapy progresses and the number of shock waves administered increases, it may be desirable to increase the frequency at which the displacement measurements are performed.

The displacement measurement can be provided to a clinician in a number of ways. For example, in at least one exemplary embodiment, the therapy system can be configured such that no additional shock waves are allowed once the displacement measurement indicates fragmentation has occurred, requiring a clinician to override this limit if additional shock wave administration is desired. In other embodiments, the displacement measurements can be provided in real-time to a clinician, so that the clinician can observe the displacement measurements and make his or her own determination as to whether therapy should be continued or terminated. The displacement measurements can be provided as part of the visual display, or can be audibly conveyed to a clinician, or both. It should also be recognized that once the displacement data had indicated that the kidney stone is fragmented, the size of the fragments can be determined using the resonant acoustic scattering frequency technique disclosed herein. Again, it should be recognized that the concepts disclosed herein are generally capable of being implemented individually, or in some desired combination.

FIG. 14B is a flow chart 130 illustrating exemplary steps for correlating a displacement of simulated kidney stone fragments induced by a pressure pulse of a known magnitude to a particular particle size, to develop the displacement based endpoint for terminating shock wave therapy in the concept noted above. In a block 132, empirical data correlates particle displacement induced by a pressure pulse of known magnitude to a particle size, using a system generally consistent with that described above with respect to FIG. 13. This technique can be achieved in several different ways. For example, the sample container can be initially filled with 2 mm particles (or some other defined size, preferably a size corresponding to a fully or substantially comminuted kidney stone), and displacement data can be collected over a range of different pressure pulses, to develop an understanding of how particles of that size are displaced by pressure pulses of known magnitudes. Alternatively, an intact simulated kidney stone can be fragmented using a system generally consistent with that described above with respect to FIG. 4, so that resonant acoustic scattering frequency spectrums are collected as the simulated stone is fragmented by the application of repeated shock waves. As discussed above, the resonant acoustic scattering frequency spectrum is a function of particle size, such that particle size during the shock wave therapy can be determined based on the frequency spectrum. At various points in the shock wave therapy, ultrasound imaging probe 122 (from FIG. 13) can be used to determine displacement data for particles of known size (the size having been determined from the resonant acoustic scattering frequency spectrum). Such data can be collected between the application of successive shock waves, which will enable empirical data to be collected that can provide a correlation between displacement data and particle size, for a pressure pulse of a specific magnitude.

Referring once again to FIG. 14B, after having collected empirical data providing such correlation, in a block 134, particle displacement monitoring is integrated into shock wave therapy, such that displacement data are collected at various times during shock wave therapy. This technique will likely increase the treatment time required for shock wave therapy (because the displacement data will need to be collected between the application of shock waves, meaning that shock waves cannot be administered as rapidly). In a block 136, once the measured displacement matches the empirical data, indicating that the kidney stone fragments are of the desired size, therapy can be terminated, or terminated after the administration of a few additional shock waves to ensure that the kidney stone is fully comminuted. It should be noted that this displacement technique can be used independent of the resonant acoustic scattering technique described above, once the correlation between size and displacement is determined. It should also be recognized that both resonant acoustic scattering and the displacement correlation described above can be employed in the same shock wave therapy regime to provide two independently determined endpoints, providing a clinician with additional indications that a kidney stone has been successfully comminuted.

As discussed above, an additional aspect of the concepts disclosed herein is the use of vibro-acoustography to reduce a dose administered to a patient during shock wave therapy, by gating the administration of shock waves, to reduce a likelihood that any single shock wave will miss a kidney stone (and thus be a wasted portion of the total dose administered). Imaging ultrasound has been used to provide such gating, with some success. Vibro-acoustography based gating represents a significant improvement, because it provides a better signal-to-noise ratio, requires less sophisticated equipment, and requires less processing (therefore, vibro-acoustography functions as a faster trigger than imaging ultrasound). It should be recognized that the term vibro-acoustography is generally employed to describe a technique wherein two acoustic sources with overlapping foci are used to produce an image. In terms of vibro-acoustography based gating, no image need be generated, rather the signal produced is used to control the administration of a shock wave. An alternate name for the technique disclosed herein would be two frequency mixing based gating.

The principles of this technique are based on using acoustic radiation force generated with vibro-acoustography to detect the position of a kidney stone. Two focused sources with overlapping foci are used to generate a dynamic radiation force within the focal region of a lithotripter. Detection of a moving kidney stone within the overlapping foci of the focus sources, and therefore within the focus of the lithotripter, is analyzed by thresholding the amplitude of the acoustic emission from the kidney stone measured with a low-frequency hydrophone receiver. If the kidney stone is detected, a shock wave will be triggered.

The use of two fundamental frequencies to generate sum and difference frequencies is understood in the art. It has been referred to also as a scattering of sound by sound, and as a parametric acoustic array. The effect was first noticed for large amplitude acoustic waves traveling in air, and in other fluids. Regarding medical acoustics, difference frequency methods have been applied to generate a dynamic radiation force that is useful for imaging where two confocal focus sources generate a force that is localized within the overlapping foci. Very small objects (sub-millimeter) can be detected by scanning through the medium surrounding the object and recording the acoustic emission at each location. High resolution is possible if the dynamic radiation force is applied at the resonance frequency of the object. An image is formed by mapping amplitude of the acoustic emission to brightness. This method, referred to as vibro-acoustography, is most useful if the object of interest has acoustic properties different than the surrounding tissue i.e. it will have a different vibration response that its background. This technique can be used both with electronic beam steering and mechanical scanning. As noted above, as used herein, no image need be generated; instead, the signal collected by the hydrophone is employed to trigger the shock wave.

The fundamental frequencies and difference frequency used in vibro-acoustography can be sufficiently low so as to be unlikely to be affected by attenuation. Higher pressure amplitudes may also be used if the pulse repetition frequency is low enough for compliance with FDA regulations for diagnostic ultrasound exposure (approximately 200 mW/cm$^2$).

Essentially, a kidney stone within the lithotripter focus, exposed to the two fundamentals and dynamic radiation force at the difference frequency, will emit a low frequency acoustic signal that can be detected and used to trigger the shock wave. Since the active volume of the difference frequency is localized within the overlapping foci of the two fundamental sources, and the overlapping foci is smaller than the lithotripter's vocal volume, a detected stone would most likely be hit by the shock wave. A higher hit rate will likely increase fragmentation efficiency for the FDA regulated number of shock waves, or perhaps reduce the number of shock waves necessary for complete fragmentation. In either case, a patient stands a higher chance of being stone free after one procedure, and may avoid the increased side effects due to multiple treatments.

FIG. 15 schematically illustrates an empirical system employed to use vibro-acoustography to trigger the application of a shock wave applied to a simulated kidney stone. The system requires the use of two separate acoustical sources 140a and 140b, each of which exhibit a focal region, with a focal region 142a corresponding to source 140a, and a focal region 142b corresponding to source 140b. Source 140a and 140b are positioned so that their focal regions overlap each other, and also overlap a focal region 148 of the shock wave source (it should be recognized that the elements of FIG. 15 are integrated into a shock wave therapy system such as that illustrated in FIGS. 2 and 3; it will be understood that elements associated with resonant acoustic scattering do not need to be implemented for therapy systems employing vibro-acoustography based gating, although in at least one exemplary embodiment, vibro-acoustography based gating and resonant acoustic scattering techniques are implemented together). The vibro-acoustography technique also utilizes a receiver 146, configured to detect an acoustical reflection of an object 144 disposed in the overlapping portion of focal regions 142a and 142b. In some exemplary embodiments, receiver 146 represents an additional receiver added to a shock wave therapy system, while in other exemplary embodiments, a shock wave therapy system may already include a receiver that can be used to implement receiver 146. Significantly, the overlapping portion of focal regions 142a and 142b is significantly smaller than the focal region of the shock wave source, and that overlapping portion is disposed well within the focal region of the shock wave source. Thus, when an object (such as a kidney stone) is detected in the overlapping portion of focal regions 142a and 142b, it will be within the focal region of the shock wave source, such that if the shock wave source is triggered immediately, the object will still likely be disposed within a focal region of the shock wave when the shock wave impacts the object. Thus, vibro-acoustography gating will reduce an amount of shock waves that miss the kidney stone.

Note that when implementing the vibro-acoustography gating technique, either a separate controller, or the therapy system's own controller would then need to be configured to analyze the collected reflection signal from the overlapping focal region, and determine when the shock wave should be triggered.

With respect to empirical studies performed using the system of FIG. 15, two focused sources with a diameter equal to 10 cm, a curvature equal to 20 cm, and $f_0$ equal to 1.1 MHz were used to generate a difference frequency. The acoustic field of one source was mapped to determine its focal dimensions, the other was assumed to be the same. A hydrophone was used to measure the field at 1 mm steps along the axis of the transducer. Beam width was measured at 0.1 mm steps at the location of maximum axial pressure amplitude. Local dimensions at −6 dB were 4×58 mm and assumed to be asymmetric (in a cigar shape).

Alignment of the sources was an iterative process. First, pointers designed to indicate the geometric focus were used to overlap the foci. Second, the angle of intersection between the axes of the sources was set at roughly 30°, which left a small space between the sources to place a receiver. Third, a long cylinder made of steel with a diameter of 6.4 mm was placed where the pointers converged. Fourth, each source was wired with a transmitter and a receiver using a diplexer, and the positions of the sources were adjusted in small increments until the amplitude of the received signals from each source was maximized, without moving the steel cylinder. Pointers were used again to verify that the axes of the sources were still in the horizontal plane.

Focal dimensions of the difference frequency were measured using backscatter from the long steel cylinder. The objective was to determine the volume through which a kidney stone sized object could be detected with the receiver. A difference frequency of 25 kHz was used ($f_1$=1.1 MHz, $f_2$=1.125 MHz), and scatter was measured with a low-frequency hydrophone (Model 8103™, Bruel & Kjer, DK-2850, Naerum, Denmark) placed between the two sources. The active area of the hydrophone was level with the overlapping foci of the sources. Geometrically, the area of overlap was approximately 4×14 mm, generally as indicated in FIG. 15. When measured, the −6 dB sensitivity of detection was approximately a 2×10 mm cigar-shaped area assumed to be asymmetric. Specular reflection from the steel cylinder may have caused the measurable focal area to be smaller than the geometric overlap, i.e., ultrasound that could have been detected with a point receiver at the focus was reflected away from the receiver placed between the sources. In terms of localizing a stone within the focus of a lithotripter, this step may be beneficial. Most importantly for targeting, the sensitive volume of the overlapping foci, termed the VA-focus (VA corresponding to vibro-acoustography), was smaller than the focal volume of the lithotripter. A stone detected within that VA-focus, which overlaps the focal volume of the lithotripter, will most likely be hit by a shock wave.

The objective of one empirical study performed in developing this technique was to stimulate stone motion and compare a non-targeted method with a VA-based targeting method. Kidney stones often move during shock wave therapy, as a result of the patient breathing and shifting. To simulate a non-targeted therapy, a total of 200 shock waves at 18 kV charging voltage were triggered at 1 Hz while a kidney stone was moved. With the VA-targeting technique, the stone was moved and a total of 200 shock waves at 18 kV charging voltage were triggered when the difference frequency was detected by the receiver. Stone motion was achieved by using a motor to move the simulated stone in one dimension in a range of approximately 4 cm. The path of the stone overlapped with the lithotripter focus for approximately 1 cm at one end of its range. Motion of the stone was periodic at 0.35 Hz, placing it within the focal region of the lithotripter for approximately 30% of the time. Stones were held loosely in a latex sleeve and position of the stone and fragments within the sleeve were not controlled.

Excitation signals for the sources were generated with function generators and power amplifiers. Pulses sent to each source were 400 µs long, delivered 50 W of electrical power, and were triggered at a repetition frequency of 10 Hz. With $f_1$=1.1 MHz and $f_2$=1.125 MHz, this test was equivalent to four cycles of the 10 kHz difference frequency, which was selected based on results from previous experiments. The positive pressure at the focus of each source was approximately 1 MPa. As noted above, the difference frequency was detected with the low-frequency hydrophone. After detection, the hydrophone signal was amplified by 50 dB, and bandpass filtered from 2 kHz to 50 kHz, time gated based on propagation distances, and displayed with a digital oscilloscope.

Each source was excited with pulses that were long enough to produce multiple cycles of the difference frequency that could be easily identified on an oscilloscope. The 400 µs long pulses corresponded to a length of 600 mm in water. Pulses can be shortened significantly, if the difference frequency was much higher, for example 100 kHz, and should produce similar results. The choice of 10 kHz for the empirical study was driven in part by parameters of the sources, which were selected simply because they were readily available, and had identical geometries. The sources were air-backed transducers made of piezoceramic material, and having a Q-value of 10. Accordingly, their ability to efficiently radiate sound is limited to a narrow bandwidth. Sources that are broadband, or that have different resonant frequencies, could be used to reduce the pulse length. Acoustic coupling or reflections did not influence the empirical study because the receiver signal was time gated and a difference frequency was only detected when the stone was within the VA focus.

After the experiments, stones were allowed to dry and were then sieved to measure fragmentation efficiency at particle sizes of less than 3 mm, less than 2 mm, and less than 1 mm. In this study, for the un-targeted shock wave therapy, 10.3% of the particles were less than 3 mm, 9.4% of the particles were less than 2 mm, and 6.5% of the particles were less than 1 mm in size, while treatment time was 3 minutes and 20 seconds. For the VA-gated/targeted shock wave therapy, 30% of the particles were less than 3 mm, 22% of the particles were less than 2 mm, and 14% of the particles were less than 1 mm in size, while treatment time was 9 minutes and 20 seconds. Significantly, vibro-acoustography targeting approximately doubled fragmentation efficiency for particles smaller than 2 mm, the size which urologists consider passable through the urinary tract. The targeted technique was twice as efficient, but took about three times as long.

FIG. 16A graphically illustrates a voltage versus time curve detected by the hydrophone in FIG. 15 when a simulated kidney stone was not within the overlapping foci, and FIG. 16B graphically illustrates a voltage versus time curve detected by the hydrophone in FIG. 15 when a simulated kidney stone was within the overlapping foci. Significantly, the amplitude in FIG. 16B is strikingly distinguishable from the amplitude in FIG. 16A.

The type of targeting discussed above improves fragmentation efficiency by a large margin over non-targeted methods simply because each shock wave hits the stone. This improvement can either lead to reduced doses or significantly increased fragmentation efficiency at the same doses. Preferably, the vibro-acoustography based gating technique will employ an excitation pulse length, a pulse repetition rate, and a peak frequency that are varied to optimize the signal, while remaining below FDA output guidelines.

FIG. 17 is a flow chart 150 of exemplary steps for reducing a dose required to comminute kidney stones by using vibro-acoustography to trigger the application of a shock wave, thereby reducing the number of shock waves that miss the kidney stone. In a block 152, vibro-acoustography data of a target area is collected to determine when a kidney stone is positioned in the overlapping focal regions of the vibro-acoustography sources and the shock wave source, generally as described above. This technique will likely increase the treatment time required for shock wave therapy (because the vibro-acoustography data will need to be collected in between the application of shock waves, meaning that shock waves cannot be administered as rapidly). However, the dosage reduction provided by the vibro-acoustography gating technique will more than offset the increased treatment time. In a decision block 154, a determination is made as to whether a kidney stone has been detected in the overlapping focal regions. If so, then in a block 156, the shock wave is triggered. Even if the kidney stone is in motion, because the shock wave can be triggered relatively quickly, and the kidney stone will be moving relatively slowly (such motion is generally attributable to respiration of or movement by the patient), it is likely that few shock waves will miss the kidney stone. If, in decision block 154, no kidney stone has been detected in the overlapping focal regions, data are once again collected from the target area until a kidney stone is detected.

In exemplary embodiments, one of the additional techniques disclosed above (i.e., detection of fragmentation by resonant acoustic scattering, detection of the endpoint for terminating therapy by resonant acoustic scattering, detection of fragmentation by displacement data, detection of the endpoint for terminating therapy by displacement data, and detection of fragmentation by pressure wave dispersal to improve image based fragmentation detection) is implemented in connection with vibro-acoustography based gating.

As discussed above, more than one of the concepts disclosed herein can be incorporated into a single shock wave therapy treatment. It should be noted that a particularly beneficial synergy is achieved when gating the administration of a shock wave using vibro-acoustography (generally as described above) is combined with monitoring the resonant acoustic scattering frequency spectrum of a kidney stone to detect an endpoint for terminating therapy (i.e., to detect a frequency that correlates to a substantially comminuted kidney stone, also as described above). One reason this synergy is particularly powerful is because without the endpoint validation provided by the resonant acoustic scattering frequency spectrum, it would be difficult to know when to terminate therapy, meaning the opportunity to reduce dosage by ensuring that very few shock waves miss the kidney stone would not be maximized. Preferably, the vibro-acoustography based gating components (a FIRE system) will be synchronized with the resonant acoustic scattering frequency components (an END system). The END system is timed to detect scatter from the shock wave, and the FIRE system is timed to avoid it. However, the END system is passive and will detect the FIRE acoustic output, but any complication this detection may create can be avoided by gating the END detectors following the trigger from the FIRE system, when the shock wave is triggered and the FIRE system is silent. A benefit to such a configuration is that the END system data indicates how many shock waves hit the stone (shock waves that do not hit the stone do not induce the resonant acoustic scattering wave), which is useful for assessing the accuracy of the FIRE system. The END system enables measuring the reduction in the FIRE signal as the stone undergoes fragmentation. The FIRE system can potentially be used to enhance the resonant scatter of kidney stone fragments, for example, by generating a wave at the resonance frequency of 2 mm kidney stone fragments to probe for kidney stone fragments of that size (or some other desired size). Note that targeting and endpoint determination have always been critical limitations of shock wave therapy. The FIRE and END systems proposed herein are practical and understandable. This makes it reasonable to expect that shock wave therapy system manufacturers will have no difficulty incorporating the FIRE and END systems in their products, and that urologists will make use of such systems. More importantly, the publishing of quantitative evidence of the benefits of these systems will make the urologist community demand endpoint and targeting systems for the health of their patients.

It should also be noted that research to this point has focused on empirical studies based on non-tissue models (i.e., no animal or human studies have been completed). To adapt the empirical systems described above for use in actual tissue, it should be recognized that the issues of signal loss in tissue, refraction in tissue, and coupling to tissue will need to be addressed. Those of ordinary skill in the art will readily recognize that such challenges are routinely addressed in the ultrasound arts, and the strategies utilized in ultrasound technologies can also be utilized to address these issues with respect to the concepts disclosed herein. Modifications to the technology described above can include, but are not limited to, employing a higher gain on the preamplifier for the resonant acoustic scattering wave receiver, using a thicker PVDF film in the resonant acoustic scattering wave receiver, employing narrowband piezo-ceramics in the resonant acoustic scattering wave receiver, employing multiple receivers in place of a single resonant acoustic scattering wave receiver. Because sound speed in soft tissue varies less than about 10%, and refraction of waves and water is small, the effects of tissue on the signal wave propagation are readily calculable (signal wave propagation for the resonant acoustic scattering signal, for the propagating waves employed in vibro-acoustography, and for the propagating waves employed in measuring displacement). Coupling acoustical receivers and transducers to tissue is well understood.

As noted above, synthetic resonant acoustic scatter data were generated in the empirical studies employed to develop the resonant acoustic scattering technology disclosed herein. A brief discussion of the model used to generate such synthetic data is briefly described below.

A model for elastic wave propagation, originally developed to determine stresses within kidney stones due to the impact of shock waves, was used to study scatter from intact and fragmented stone models. First, pressure and mechanical stresses in the stone were calculated numerically with the linear elastic model, where the underlying equations were Newton's second Law and Hooke's Law.

$$\frac{\partial v_i}{\partial t} = \frac{1}{\rho_0} \frac{\partial \tau_{ij}}{\partial x_j} \quad (3)$$

$$\frac{\partial \tau_{ij}}{\partial t} = \lambda \delta_{ij} \frac{\partial v_k}{\partial x_k} + \mu \left( \frac{\partial v_i}{\partial x_j} + \frac{\partial v_j}{\partial x_j} \right) \quad (4)$$

Eqs. (3) and (4) are written in index notation, where $v_i$ represents the velocity at each location, $\tau_{ij}$ represents the stress tensor, $\delta_{ij}$ represents the Kronecker delta function, $\rho_0$ is the material density, and $\lambda$ and $\mu$ are the Lame coefficients of the material. The equations were cast in cylindrical coordinates and solved using a finite difference grid that was staggered in both time and space, referred to as the Viruex scheme in geophysics, or the Yee cell in electromagnetics. The asymmetric numerical grid was initialized with a planar shock wave and elastic coefficients representing the stone and surrounding water. Material properties necessary for simulation are summarized in the table shown in FIG. 18. Radiation from the stone was calculated with the Helmholtz-Kirchoff integral taken on a surface surrounding the stone. Scatter was calculated by averaging acoustic pressure over a surface representing a spherical receiver at a distance of 150 mm from the stone model.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

The invention in which an exclusive right is claimed is defined by the following:

1. A method for detecting the fragmentation of a kidney stone during shock wave therapy, the method comprising the steps of:
    (a) detecting a resonant acoustic scattering wave to generate a resonant acoustic scattering signal during therapy, the resonant acoustic scattering signal being indicative of internal stress vibrations in the kidney stone, where the internal stress vibrations are in response to shock waves impacting the kidney stone;
    (b) processing the resonant acoustic scattering signal to determine a frequency spectrum of the stress vibrations, the processing comprising determining a frequency spectrum of the stress vibrations induced by an initial shock wave, and determining a frequency spectrum of the stress vibrations induced by at least one subsequent shock wave; and
    (c) monitoring the frequency spectrum of the stress vibrations during therapy in order to determine if the kidney stone is fragmented, the monitoring comprising: comparing the frequency spectrum of the stress vibrations induced by the initial shock wave with the frequency spectrum of the stress vibrations induced by the at least one subsequent shock wave to detect a change in the frequency spectrum, the change in the frequency spectrum being indicative of fragmentation.

2. The method of claim 1, wherein:
    the step of monitoring the frequency spectrum of the stress vibrations during therapy in order to determine when the kidney stone is fragmented comprises the step of dividing the frequency spectrum of the stress vibrations induced by the at least one subsequent shock wave by the frequency spectrum of the stress vibrations induced by the first shock wave to determine a frequency ratio indicative of a change in size of the kidney stone, wherein a frequency ratio greater than two is indicative that the kidney stone has fragmented.

3. The method of claim 1, further comprising the step of determining when the frequency spectrum of the stress vibrations is indicative of kidney stone fragments of a specific size, the frequency spectrum of the stress vibrations being a function of a speed of sound in the kidney stone and the specific size.

4. The method of claim 3, wherein the speed of sound in the kidney stone is estimated.

5. The method of claim 3, wherein the speed of sound in the kidney stone is empirically determined.

6. The method of claim 1, further comprising the step of determining when a frequency of the stress vibrations reaches 750 kHz, such a frequency being indicative that the kidney stone is comminuted.

7. The method of claim 1, further comprising the step of gating the administration of shock waves using a targeting paradigm based on vibro-acoustography, thereby minimizing a number of shock waves that miss the kidney stone, and enhancing an efficiency of the shock wave therapy.

8. The method of claim 1, wherein the step of detecting a resonant acoustic scattering wave comprises the step of detecting the resonant acoustic scattering wave using at least one detector configuration selected from the group consisting of:
    (a) a broadband detector;
    (b) a narrowband detector; and
    (c) a plurality of detectors.

9. The method of claim 1, wherein the step of processing the resonant acoustic scattering signal to determine a frequency spectrum of the stress vibrations comprises the steps of:
(a) filtering the resonant acoustic scattering signal with a high pass filter to remove transient low frequency artifacts caused by a source of the shock waves; and
(b) de-convolving the filtered acoustic signal to remove artifacts induced by the step of filtering.

10. The method of claim 1, further comprising the steps of:
(a) confirming that the kidney stone has fragmented by irradiating the kidney stone fragments with an acoustic pressure wave of a known magnitude;
(b) determining a displacement of the kidney stone fragments induced by the acoustic pressure wave, a magnitude of the displacement being a function of the size of the kidney stone fragments, with relatively larger fragments experiencing relatively smaller displacements; and
(c) comparing the displacement determined with a displacement corresponding to an intact kidney stone, to determine whether the kidney stone has been fragmented.

11. The method of claim 10, wherein the step confirming that the kidney stone has fragmented by irradiating the kidney stone fragments with an acoustic pressure wave of a known magnitude comprises one of the following steps:
(a) using an acoustic pressure source to produce the acoustic pressure wave, wherein said acoustic pressure source is disposed along a shock wave axis of the shock waves used in the therapy; and
(b) using an acoustic pressure source to produce the acoustic pressure wave, wherein said acoustic pressure source is disposed at an angle relative to a shock wave axis of the shock waves used in the therapy, and disposed outside of an acoustic path of the shock waves.

12. The method of claim 1, further comprising the step of administering an acoustic pressure pulse during the shock wave therapy, for a function other than fragmenting the kidney stone that is selected from the group consisting of:
(a) using the acoustic pressure pulse to determine a displacement of the kidney stone, in order to determine whether the kidney stone has fragmented;
(b) using the acoustic pressure pulse to determine a displacement of kidney stone fragments, in order to determine whether the kidney stone has been comminuted;
(c) using the acoustic pressure pulse to disperse kidney stone fragments, thereby enabling imaging modalities to more clearly differentiate fragmented kidney stones from intact kidney stones; and
(d) using the acoustic pressure pulse to disperse kidney stone fragments, thereby facilitating passage of the kidney stone fragments from the kidney.

13. A system for providing shock wave therapy to comminute a kidney stone, the system being configured to detect fragmentation of the kidney stone, the system comprising:
(a) a shock wave source;
(b) an acoustic receiver configured to detect a resonant acoustic scattering signal during therapy, the resonant acoustic scattering signal being indicative of internal stress vibrations in the kidney stone, where the internal stress vibrations are produced in response to shock waves impacting the kidney stone;
(c) means for processing the resonant acoustic scattering signal to determine a frequency spectrum of the stress vibrations produced in response to an initial shock wave and to determine a frequency spectrum of the stress vibrations produced in response to at least one subsequent shock wave; and
(d) means for monitoring the frequency spectrum of the stress vibrations during therapy in order to determine when the kidney stone is fragmented, the means for monitoring including means for comparing the frequency spectrum of the stress vibrations produced in response to the initial shock wave with the frequency spectrum of the stress vibrations produced in response to the at least one subsequent shock wave.

14. A kit for use with a system for providing shock wave therapy to comminute a kidney stone, the kit comprising:
(a) means to detect a resonant acoustic scattering wave and generate a resonant acoustic scattering signal during therapy, the resonant acoustic scattering signal being indicative of internal stress vibrations in the kidney stone, where the internal stress vibrations are in response to shock waves impacting the kidney stone; and
(b) means to analyze the resonant acoustic scattering signal during therapy to determine whether the kidney stone has fragmented or is comminuted,
wherein the means to analyze the resonant acoustic scattering signal includes:
means for determining a frequency spectrum of the internal stress vibrations induced by each of an initial shock wave and at least one subsequent shock wave; and
means for comparing the frequency spectrum induced by the initial shock wave with the frequency spectrum induced by the at least one subsequent shock wave to detect a change in the frequency spectrum, the change in the frequency spectrum being indicative of kidney stone fragmentation.

15. The kit of claim 14, wherein the means to analyze the resonant acoustic scattering signal comprises a memory medium on which are stored machine executable instructions for carrying out the step of determining whether the kidney stone has fragmented or is comminuted.

16. The kit of claim 14, wherein the means to analyze the resonant acoustic scattering signal comprises a controller configured to carry out the step of determining whether the kidney stone has fragmented or is comminuted.

17. The method of claim 1, further comprising the step of detecting a shock wave reflection from the kidney stone prior to detecting the resonant acoustic scattering wave; and
detecting an acoustic signal corresponding to cavitation from adjacent the kidney stone after detecting the resonant acoustic scattering wave.

18. The method of claim 17, wherein the processing of the resonant acoustic scattering signal is performed in response to a timing of the resonant acoustic scattering signal.

19. The method of claim 18, wherein the shock wave reflection is generated in less than 5 µs after a shockwave impacts the kidney stone, the resonant acoustic scattering wave is generated after the shock wave between 5 µs and 20 µs, and the acoustic signal corresponding to cavitation is generated after the shock wave between about 20 µs and 350 µs.

20. The method of claim 19, wherein the means for processing determines the frequency spectrums using signals generated between 5 µs and 250 µs after the shockwave.

* * * * *